US008956835B2

(12) United States Patent
Nakas et al.

(10) Patent No.: US 8,956,835 B2
(45) Date of Patent: Feb. 17, 2015

(54) METHODS FOR PRODUCING POLYHYDROXYALKANOATES FROM BIODIESEL-GLYCEROL

(75) Inventors: James P. Nakas, Lafayette, NY (US); Chengjun Zhu, Syracuse, NY (US); Joseph A. Perrotta, Liverpool, NY (US); Christopher T. Nomura, Syracuse, NY (US)

(73) Assignee: Suny Research Foundation, Albany, NY (US)

( * ) Notice: Subject to any disclaimer, the term of this patent is extended or adjusted under 35 U.S.C. 154(b) by 0 days.

(21) Appl. No.: 13/303,856

(22) Filed: Nov. 23, 2011

(65) Prior Publication Data

US 2012/0135480 A1 May 31, 2012

Related U.S. Application Data

(60) Provisional application No. 61/417,004, filed on Nov. 24, 2010.

(51) Int. Cl.
C12P 7/42 (2006.01)
C12P 7/62 (2006.01)
C12P 7/00 (2006.01)
C12P 7/40 (2006.01)

(52) U.S. Cl.
CPC . *C12P 7/625* (2013.01); *Y02E 50/13* (2013.01)
USPC ............. 435/135; 435/148; 435/41; 435/132; 435/147

(58) Field of Classification Search
None
See application file for complete search history.

(56) References Cited

U.S. PATENT DOCUMENTS

| | | | |
|---|---|---|---|
| 5,871,980 A | 2/1999 | Naylor et al. | |
| 5,973,100 A * | 10/1999 | Asrar et al. | 528/176 |
| 6,316,262 B1 | 11/2001 | Huisman et al. | |
| 6,593,116 B1 | 7/2003 | Huisman et al. | |
| 2006/0105439 A1 | 5/2006 | Nakas et al. | |

OTHER PUBLICATIONS

Verlinder, RA; et al; "Bacterial synthesis of biodegradable polyhydroxyalkanoates" Journal of Applied Microbiology, 102, 1437-1449, 2007.*
Chung, Sun Ho; et al; "Effect of Levulinic Acid on the Production of Poly(3-hydroxybutyrate-co-3-hydroxyvalerate) by *Ralstonia eutropha* KHB-8862" The Journal of Microbiology, 39, 79-82, 2001.*
da Silva, Gervasio Paulo; et al; "Glycerol: A promising and abundant carbon source for industrial microbiology" Biotechnology Advances, 27, 30-39, 2009.*
Aldor and Keasling 2001, Metabolic engineering of poly(3-hydroxybutyrate-co-3-hydroxyvalerate) composition in recombinant *Salmonella enterica* serovar typhimurium, Biotechnology and Bioengineering 76(2):108-14.
Almeida AD, Nikel PI, Giordano AM, Pettinari MJ. Effects of granule-associated protein PhaP on glycerol-dependent growth and polymer production in poly(3-hydroxybutyrate)-producing *Escherichia coli*. Appl. Environ. Microbiol. 2007;73: 7912-7916.
Amara AA, Steinbuchel A, Rehm BH. In vivo evolution of the *Aeromonas punctata* polyhydroxyalkanoate (PHA) synthase: isolation and characterization of modified PHA synthases with enhanced activity. *Appl Microbiol Biotechnol*. 2002;59:477-482.
Anderson AJ, Dawes EA. Occurrence, metabolism, metabolic role, and industrial uses of bacterial polyhydroxyalkanoates. *Microbiol Rev*. 1990; 54:450-72.
Aoyagi Y, Doi Y, Iwata T. Mechanical properties and highly ordered structure of ultra-high-molecular weight poly[(R)-3-hydroxybutyrate] films: effects of annealing and two-step drawing. Polym Degrad Stab. 2003;79:209-216).
Ashby RD, Solaiman DK, Foglia TA. Synthesis of short-/medium-chain-length poly(hydroxyalkanoate) blends by mixed culture fermentation of glycerol. *Biomacromolecules*. 2005; 6:2106-2112.
Cao, Amin, Ken-ichi Kasuya, Hideki Abe, Yoshiharu Doi and Yoshio Inoue. Studies on comonomer compositional distribution of the bacterial poly(3-hydroxybutyric acid-co-3-hydroxypropionic acid)s and crystal and thermal characteristics of their fractionated component copolyesters. Polymer, 1998, 39 (20): 4801-4816.
Cavalheiro JMBT, Dealmeida MCMD, Grandfils C, Dafonseca MMR. Poly(3-hydroxybutyrate) production by *Cupriavidus necator* using waste glycerol. Process Biochem. 2009;44:509-515.
Choi JI, Lee SY. Process analysis and economic evaluation for poly(3-hydroxybutyrate) production by fermentation. *Bioprocess Eng*. 1997;17:335-342.
Choi J, Lee SY. Factors affecting the economics of polyhydroxyalkanoate production by bacterial fermentation. *Appl Microbiol and Biotechnol*. 1999;51:13-21.
Choi et al. 1998, Cloning of the *Alcaligenes latus* polyhydroxyalkanoate biosynthesis genes and use of these genes for enhanced production of poly(3-hydroxybutyrate) in *Escherichia coli*, Appl. Environ. Microbiol. 64, 4897-4903.

(Continued)

*Primary Examiner* — Blaine Lankford
*Assistant Examiner* — David Berke-Schlessel
(74) *Attorney, Agent, or Firm* — Harris Beach PLLC

(57) ABSTRACT

Methods are provided for producing biodegradable polyhydroxyalkanoates (PHAs) with desired geometry, molecular mass, mechanical and/or physical-chemical properties from glycerol, an inexpensive carbon source and byproduct of the biodiesel industry. Microorganisms capable of converting carbon to PHA can be used to convert biodiesel-glycerol to poly-3-hydroxybutyrate (PHB) or other monomer or copolymer PHAs via fermentation. The microorganisms are cultured in a medium comprising glycerol as a primary carbon source and one or more low molecular mass organic acids as a secondary carbon source. Biomass can be harvested from the culture medium and crude PHA extracted and purified, thereby recovering purified PHA with the desired property. After PHA isolation, a nucleating agent can be added to improve certain physical-chemical properties of the PHA, e.g., crystallization temperature, to enhance performance of the PHA during injection molding.

13 Claims, 11 Drawing Sheets

(56) References Cited

OTHER PUBLICATIONS

Gerngross TU, Martin DP. Enzyme-catalyzed synthesis of poly[(R)-(−)-3-hydroxybutyrate]: Formation of macroscopic granules in vitro. *Proc Natl Acad Sci U S A*. 1995;92:6279-6283.

Gouda MK, Swellam AE, Omar SH. Production of PHB by a *Bacillus megaterium* strain using sugarcane molasses and corn steep liquor as sole carbon and nitrogen sources. *Microbiol Res*. 2001;156:201-207.

Jacquel, Nicolas, Chi-Wei Lo, Yu-Hong Wei, Ho-Shing Wu and Shaw S. Wang. 2008. Isolation and purification of bacterial poly(3-hydroxyalkanoates). Biochemical Engineering Journal, 39: 15-27.

Keenan TM, Nakas JP, Tanenbaum SW. Polyhydroxyalkanoate copolymers from forest biomass. *J Ind Microbiol Biotechnol*. 2006;33:616-626.

Keenan TM, Tanenbaum SW, Stipanovic AJ, Nakas JP. Production and characterization of poly-beta-hydroxyalkanoate copolymers from *Burkholderia cepacia* utilizing xylose and levulinic acid. *Biotechnol Prog*. 2004;20:1697-1704.

Kessler, B., R. Weusthuis, B. Witholt, G. Eggink. 2001. Production of Microbial Polyesters: Fermentation and Downstream Processes. Advances in Biochemical Engineering/Biotechnology, 71: 159-182.

Koller M, Bona R, Braunegg G, Hermann C, Horvat P, Kroutil M, Martinz J, Neto J, Pereira L, Varila P. Production of polyhydroxyalkanoates from agricultural waste and surplus materials. *Biomacromolecules*. 2005;6:561-565.

Kunioka, Masao, Akira Tamaki, Yoshiharu Doi. Crystalline and thermal properties of bacterial copolyesters: poly(3-hydroxybutyrate-co-3-hydroxyvalerate) and poly(3-hydroxybutyrate-co-4-hydroxybutyrate). Macromolecules, 1989, 22 (2): 694C697.

Lütke-Eversloh, Tina, Klaus Bergander, Heinrich Luftmann, and Alexander Steinbüchel. Biosynthesis of Poly(3-hydroxybutyrate-co-3-mercaptobutyrate) as a Sulfur Analogue to Poly(3-hydroxybutyrate) (PHB). Biomacromolecules, 2001, 2 (3): 1061-1065.

Madison LL, Huisman GW. Metabolic engineering of poly(3-hydroxyalkanoates): from DNA to plastic. *Microbiol Mol Biol Rev*. 1999; 63:21-53.

Madden LA, Anderson AJ, Shah DT, Asrar J. Chain termination in polyhydroxyalkanoate synthesis: involvement of exogenous hydroxy-compounds as chain transfer agents. *Int J Biologl Macromol*. 1999;25:43-53.

Martina M, Hutmacher DW. Biodegradable polymers applied in tissue engineering research: a review. *Polym Int*. 2007;56:145-157.

Mothes G, Schnorpfeil C, Ackermann JU. Production of PHB from crude glycerol. Eng Life Sci. 2007;7:475-479.

Nikel P, Pettinari J, Mendez B. Poly(3-hydroxybutyrate) synthesis in microaerobic fed-batch cultures by a recombinant *Escherichia coli* arcA mutant using glycerol as a carbon source, J. Biotechnol. 2007;131:S157-S158.

Pachauri N, He B. Value-added utilization of crude glycerol from biodiesel production: a survey of current research activities. American Society of Agricultural and Biological Engineering Annual International Meeting, Portland, Oregon, Jul. 9-12, 2006.

Papanikolaou S. et al., Biotechnological valorization of raw glycerol discharged after bio-diesel (fatty acid methyl esters) manufacturing process; production of 1,3-propanediol, citric acid and single cell oil, Biomass Bioenergy, 2007; 32:60-71.

Rehm BH, Steinbuchel A. Biochemical and genetic analysis of PHA synthases and other proteins required for PHA synthesis. *Int J Biol Macromol*. 1999;25:3-19.

Ren Q, De Roo G, Van Beilen JB, Zinn M, Kessler B, Witholt B. Poly(3-hydroxy-alkanoate) polymerase synthesis and in vitro activity in recombinant *Escherichia coli* and *Pseudomonas putida*. *Appl Microbiol Biotechnol*. 2005;69:286-292.

Sim SJ, Snell KD, Hogan SA, Stubbe J, Rha C, Sinskey AJ. PHA synthase activity controls the molecular weight and polydispersity of polyhydroxybutyrate in vivo. *Nat Biotechnol*. 1997;15: 63-67.

Schubert et al. 1998, Cloning of the *Alcaligenes eutrophus* poly-β-hydroxybutyrate synthetic pathway and synthesis of PHB in *Escherichia coli*. J. Bacteriol. 170, 5837-5847.

Slater S, Houmiel KL, Tran M, Mitsky TA, Taylor NB, Padgette SR, Gruys KJ. Multiple β-ketothiolases mediate poly(β-hydroxyalkanoate) copolymer synthesis in *Ralstonia eutropha*. *J Bacteriol*. 1998;180:1979-1987.

Schmack G, Gorenflo V, Steinbuchel A. 1998. Biotechnological production and characterization of polyesters containing 4-hydroxyvaleric acid and medium-chain-length-hydroxyalkanoic acids. Macromolecules 31:644-649.

Steinbuchel A, Valentin HE. Diversity of bacterial polyhydroxyalkanoic acids. *FEMS Microbiol Lett*. 1995; 128:219-228.

Sudesh K, Abe H, Doi Y. Synthesis, structure and properties of polyhydroxyalkanoates: biological polyesters. *Prog Polym Sci*. 2000; 25:1503-1555.

Taidi B, Anderson AJ, Dawes EA, Byrom D. Effect of carbon source and concentration on the molecular-mass of poly(3-Hydroxybutyrate) produced by *Methylobacterium extorquens* and *Alcaligenes eutrophus*. *Appl Microbiol Biotechnol*. 1994;40:786-790.

Tanadchangsaeng, Nuttapol, Asahi Kitagawa, Tetsuya Yamamoto, Hideki Abe and Takeharu Tsuge. Identification, Biosynthesis, and Characterization of Polyhydroxyalkanoate Copolymer Consisting of 3-Hydroxybutyrate and 3-Hydroxy-4-methylvalerate. Biomacromolecules, 2009, 10 (10): 2866C2874.

Tsuge T, Fukui T, Matsusaki H, Taguchi S, Kobayashi G, Ishizaki A, Doi Y. Molecular cloning of two (R)-specific enoyl-CoA hydratase genes from *Pseudomonas aeruginosa* and their use for polyhydroxyalkanoate synthesis. *FEMS Microbiol Lett*. 1999; 184:193-198.

Vandamme P, Holmes, B, Vancanneyt M, Coenye, T, Hoste B, Coopman R, Revets H, Lauwers S, Gillis M, Kersters K, Govan JR. Occurrence of multiple genomovars of *Burkholderia cepacia* in cystic fibrosis patients and proposal of *Burkholderia multivorans* sp. nov. *Int J Syst Bacteriol*. 1997;47:1188-1200).

Yang, Taek Ho, Tae Wan Kim, Hye Ok Kang, Sang-Hyun Lee, Eun Jeong Lee, Sung-Chul Lim, Sun Ok Oh, Ae-Jin Song, Si Jae Park, Sang Yup Lee. Biosynthesis of polylactic acid and its copolymers using evolved propionate CoA transferase and PHA synthase. Biotechnology and Bioengineering, 2010, 105 (1): 150-160.

Yeh Ji, Chinte U, Du S. Structure of glycerol-3-phosphate dehydrogenase, an essential monotopic membrane enzyme involved in respiration and metabolism. *Proc Natl Acad Sci U S A*. 2008;105:3280-3285.

Yellore V, Desai A. Production of poly-3-hydroxybutyrate from lactose and whey by *Methylobacterium* sp. ZP24. *Lett Appl Microbiol*. 1998;26:391-39.

Yu, Jian, Lilian X. L. Chen. 2006. Cost-Effective Recovery and Purification of Polyhydroxyalkanoates by Selective Dissolution of Cell Mass. Biotechnology Progress, 2006, 22: 547-553.

\* cited by examiner

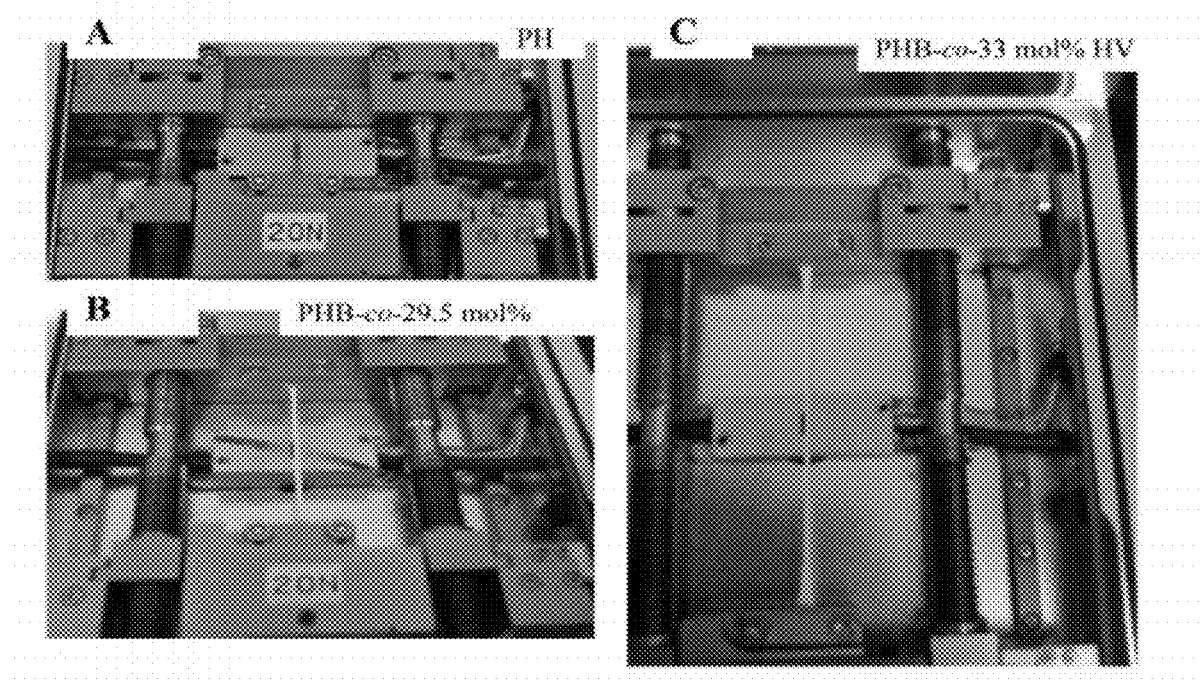
FIGS. 11A-C

METHODS FOR PRODUCING POLYHYDROXYALKANOATES FROM BIODIESEL-GLYCEROL

CROSS-REFERENCE TO RELATED APPLICATIONS

This application claims priority to and the benefit of U.S. provisional patent application Ser. No. 61/417,004, entitled "Methods for Producing Polyhydroxyalkanoates from Biodiesel-Glycerol," filed Nov. 24, 2010, which is incorporated herein by reference in its entirety.

TECHNICAL FIELD

The present invention relates to methods for producing polyhydroxyalkanoates from carbon sources using fermentation by microorganisms. The invention further relates to methods for producing biodegradable polymers from inexpensive carbon sources.

BACKGROUND OF THE INVENTION

Polyhydroxyalkanoates (PHAs) are accumulated as microbial intracellular carbon and energy reserves. These polymers represent a class of compounds with physical-chemical characteristics similar to petroleum-derived plastics such as polypropylene, polyethylene and polystyrene, but are environmentally compatible and totally biodegradable to carbon dioxide and water (Anderson A J, Dawes E A. Occurrence, metabolism, metabolic role, and industrial uses of bacterial polyhydroxyalkanoates. Microbiol Rev. 1990; 54:450-72; Madison L L, Huisman G W. Metabolic engineering of poly (3-hydroxyalkanoates): from DNA to plastic. Microbiol Mol Biol Rev. 1999; 63:21-53; Sudesh K, Abe H, Doi Y. Synthesis, structure and properties of polyhydroxyalkanoates: biological polyesters. Prog Polym Sci. 2000; 25:1503-1555). A number of microorganisms, including Ralstonia eutropha, Alcaligenes latus and several species of Pseudomonas (Choi J I, Lee S Y. Process analysis and economic evaluation for poly(3-hydroxybutyrate) production by fermentation. Bioprocess Eng. 1997; 17:335-342; Ren Q, De Roo G, Van Beilen J B, Zinn M, Kessler B, Witholt B. Poly(3-hydroxy-alkanoate) polymerase synthesis and in vitro activity in recombinant Escherichia coli and Pseudomonas putida. Appl Microbiol Biotechnol. 2005; 69:286-292; Slater S, Houmiel K L, Tran M, Mitsky T A, Taylor N B, Padgette S R, Gruys K J. Multiple β-ketothiolases mediate poly(β-hydroxyalkanoate) copolymer synthesis in Ralstonia eutropha. J Bacteriol. 1998; 180: 1979-1987; Tsuge T, Fukui T, Matsusaki H, Taguchi S, Kobayashi G, Ishizaki A, Doi Y. Molecular cloning of two (R)-specific enoyl-CoA hydratase genes from Pseudomonas aeruginosa and their use for polyhydroxyalkanoate synthesis. FEMS Microbiol Lett. 1999; 184:193-198), have been shown to produce various polyesters with different subunits (Steinbuchel A, Valentin H E. Diversity of bacterial polyhydroxyalkanoic acids. FEMS Microbiol Lett. 1995; 128:219-228). The homopolymer PHB and the copolymer poly-3-hydroxybutyrate-co-poly-3-hydroxyvalerate (PHB-co-PHV) are the most widely studied and have been produced commercially to manufacture some finished products, which are primarily used in medical applications such as tissue engineering (Martina M, Hutmacher D W. Biodegradable polymers applied in tissue engineering research: a review. Polym Int. 2007; 56:145-157). Burkholderia (formerly Pseudomonas) cepacia has been shown to efficiently synthesize short-chain-length (scl) PHAs, such as PHB, PHV, and PHB-co-PHV. By incorporating PHV with PHB to form the copolymer, lower crystallinity and better elongation can be obtained which have been shown to exhibit more desirable mechanical properties (Keenan T M, Tanenbaum S W, Stipanovic A J, Nakas J P. Production and characterization of poly-beta-hydroxyalkanoate copolymers from Burkholderia cepacia utilizing xylose and levulinic acid. Biotechnol Prog. 2004; 20:1697-1704).

Many carbon sources, including xylose, galactose, glucose, glycerol and levulinic acid, have been used to support growth and scl-PHA production by B. cepacia (Keenan T M, Tanenbaum S W, Stipanovic A J, Nakas J P. Production and characterization of poly-beta-hydroxyalkanoate copolymers from Burkholderia cepacia utilizing xylose and levulinic acid. Biotechnol Prog. 2004; 20:1697-1704; Vandamme P, Holmes, B, Vancanneyt M, Coenye, T, Hoste B, Coopman R, Revets H, Lauwers S, Gillis M, Kersters K, Govan J R. Occurrence of multiple genomovars of Burkholderia cepacia in cystic fibrosis patients and proposal of Burkholderia multivorans sp. nov. Int J Syst Bacteriol. 1997; 47:1188-1200). Although it is feasible for these carbon sources to be used to produce PHAs in the laboratory, high production costs hamper large-scale commercial production and the cost of fermentation feedstocks can account for up to 50% of the overall production cost (Choi J I, Lee S Y. Process analysis and economic evaluation for poly(3-hydroxybutyrate) production by fermentation. Bioprocess Eng. 1997; 17:335-342; Choi J, Lee S Y. Factors affecting the economics of polyhydroxyalkanoate production by bacterial fermentation. Appl Microbiol and Biotechnol. 1999; 51:13-21). Several process stream feedstocks, such as cheese whey permeate (Yellore V, Desai A. Production of poly-3-hydroxybutyrate from lactose and whey by Methylobacterium sp. ZP24. Lett Appl Microbiol. 1998; 26:391-39), wood hydrolysate (Keenan T M, Nakas J P, Tanenbaum S W. Polyhydroxyalkanoate copolymers from forest biomass. J Ind Microbiol Biotechnol. 2006; 33:616-626), sugarcane molasses and corn steep liquor (Gouda M K, Swellam A E, Omar S H. Production of PHB by a Bacillus megaterium strain using sugarcane molasses and corn steep liquor as sole carbon and nitrogen sources. Microbiol Res. 2001; 156:201-207), have been used to produce PHAs in an attempt to reduce production costs.

Glycerol (approximately 10% of the final weight of biodiesel) (Pachauri N, He B. Value-added utilization of crude glycerol from biodiesel production: a survey of current research activities. American Society of Agricultural and Biological Engineering Annual International Meeting, Portland, Oreg., 9-12 Jul., 2006) is the major byproduct of the biodiesel industry. As biodiesel production has increased dramatically from 500,000 gallons in 1999 to 450 million gallons in 2007 (National Biodiesel Board, 2008), crude glycerol generated from the transesterification of vegetable oil has also been produced in large quantities. Recent publications by Mothes et al. (Mothes G, Schnorpfeil C, Ackermann J U. Production of PHB from crude glycerol. Eng Life Sci. 2007; 7:475-479) and Cavalheiro et al. (Cavalheiro J M B T, Dealmeida M C M D, Grandfils C, Dafonseca M M R. Poly(3-hydroxybutyrate) production by Cupriavidus necator using waste glycerol. Process Biochem. 2009; 44:509-515) described direct fermentation of biodiesel-glycerol to PHB by Cupriavidus necator with polymer production approaching 50% of dry microbial biomass. In addition, Papanikolaou et al. (Papanikolaou S, Fakas S, Fick M, Chevalot I, Galiotou-Panayotou M, Komaitis M, Marc I, Aggelis G. Biotechnological valorization of raw glycerol discharged after bio-diesel (fatty acid methyl esters) manufacturing process: production of 1,3-propanediol, citric acid and single cell oil. Biomass Bioenergy 2007; 32:60-71) demonstrated the production of 1,3-propanediol, citric acid, and cellular lipids (single-cell oil) from biodiesel-glycerol using three separate microbial fermentations. Despite the commercial use of glycerol in the food, pharmaceutical, cosmetics and other industries (Pachauri N, He B. Value-added utilization of crude glycerol from biodiesel production: a survey of current research activities. American Society of Agricultural and Biological Engineering Annual International Meeting, Portland, Oreg., 9-12 Jul., 2006), it is expensive to refine crude glycerol to the purity needed for these applications.

Citation or identification of any reference in Section 2, or in any other section of this application, shall not be considered an admission that such reference is available as prior art to the present invention.

SUMMARY OF THE INVENTION

A method is provided for producing polyhydroxyalkanoate (PHA) with a desired geometry, molecular mass, mechanical and/or physical-chemical property by microbial fermentation. In one embodiment, the method comprises the steps of:

(a) providing a culture medium, wherein the culture medium comprises: glycerol as primary carbon source and one or more low molecular mass organic acids as secondary carbon source;

(b) culturing a microorganism that converts carbon to PHA in the culture medium;

(c) harvesting biomass from the culture medium;

(d) extracting crude PHA from the harvested biomass; and (e) purifying PHA from the crude PHA, thereby recovering purified PHA with the desired geometry, molecular mass, mechanical and/or physical-chemical property.

In another embodiment, the low molecular mass organic acid can include, but is not limited to, levulinic acid, propionic acid, valeric acid, dodecanoic acid, decanoic acid, octanoic acid, oleic acid and oleate In another embodiment, the glycerol is biodiesel-glycerol.

In another embodiment, the purity of the biodiesel-glycerol is 34-92%.

In another embodiment, the biodiesel-glycerol comprises less than 0.05% methanol.

In another embodiment, the culture medium can comprise xylose. In a specific embodiment, the xylose is derived from wood hydrolysate.

In another embodiment, the method further comprises, after step (e), the step of:

(f) adding a nucleating agent to the purified PHA in an amount sufficient to generate the desired geometry, molecular mass, mechanical and/or physical-chemical property in the purified PHA.

In another embodiment, the nucleating agent is talc.

In another embodiment, the PHA produced is a copolymer comprising butyric acid and valeric acid.

In another embodiment, the microorganism is selected from the group consisting of *Burkholderia cepacia, Ralstonia eutropha, Alcaligenes latus, Paracoccus denitrificans, Cupriavidus necator; Methylobacterium rhodesianum, Pseudomonas corrugata, Pseudomonas oleovorans* and *Pseudomonas putida*.

In another embodiment, the PHA with the desired geometry, molecular mass, mechanical and/or physical-chemical property is a PHA copolymer of a plurality of different PHA polymers in a desired ratio. The ratio of glycerol to the secondary carbon source in the culture medium can be predetermined (or determined to be sufficient), using methods known in the art, to produce the desired ratio of different PHA polymers in the PHA copolymer.

In another embodiment, the PHA with the desired geometry, molecular mass, mechanical and/or physical-chemical property is a PHA copolymer of butyric acid and valeric acid in a desired ratio, the secondary carbon source is levulinic acid, and the ratio of glycerol to levulinic acid in the culture medium is predetermined (or sufficient) to produce the desired ratio of butyric acid and valeric acid in the PHA copolymer.

In another embodiment, the mechanical property is increased elongation-to-break or resistance to breaking.

In another embodiment, the physical-chemical property is increased crystallization temperature.

A method is also provided for producing poly-hydroxybutyric acid (PHB) comprising the steps of:

(a) providing a culture medium, wherein the culture medium comprises glycerol as primary carbon source, (b) culturing a microorganism that converts carbon to PHA in the culture medium;

(c) harvesting biomass from the culture medium;

(d) extracting crude PHA from the harvested biomass; and (e) purifying PHA from the crude PHA.

A method is also provided for producing a desired geometry, molecular mass, mechanical and/or physical-chemical property in a PHA polymer comprising the steps of:

(a) providing a culture medium, wherein the culture medium comprises a carbon source other than glycerol (non-glycerol carbon source), e.g., xylose, as primary carbon source;

(b) culturing a microorganism that converts carbon to PHA in the culture medium to produce PHA polymer chains;

(c) adding glycerol to the culture medium in an amount sufficient to end-cap the PHA polymer chains to produce the desired geometry, molecular mass, mechanical and/or physical-chemical property in the end-capped PHA polymer;

(d) further culturing the microorganism in the culture medium with added glycerol to produce the desired geometry, molecular mass, mechanical and/or physical-chemical property in the end-capped PHA polymer;

(e) harvesting biomass from the culture medium;

(f) extracting crude PHA from the harvested biomass; and (g) purifying PHA from the crude PHA, thereby recovering end-capped PHA polymer having the desired geometry, molecular mass, mechanical and/or physical-chemical property.

BRIEF DESCRIPTION OF THE DRAWINGS

The present invention is described herein with reference to the accompanying drawings, in which similar reference characters denote similar elements throughout the several views. It is to be understood that in some instances, various aspects of the invention may be shown exaggerated or enlarged to facilitate an understanding of the invention.

FIGS. 11A-C. Real-time photographic images of stretching for different types of PHAs in tensile testing. A) shows PHB homopolymer, of which the dogbone was stretched for less than 0.7 mm to break. B) shows PHB-co-29.5 mol % HV, of which the dogbone was stretched for approximately 35 mm to break. C) shows PHB-co-33 mol % HV, of which the dogbone was stretched for approximately 66 mm to break.

DETAILED DESCRIPTION OF THE INVENTION

Figure 1:
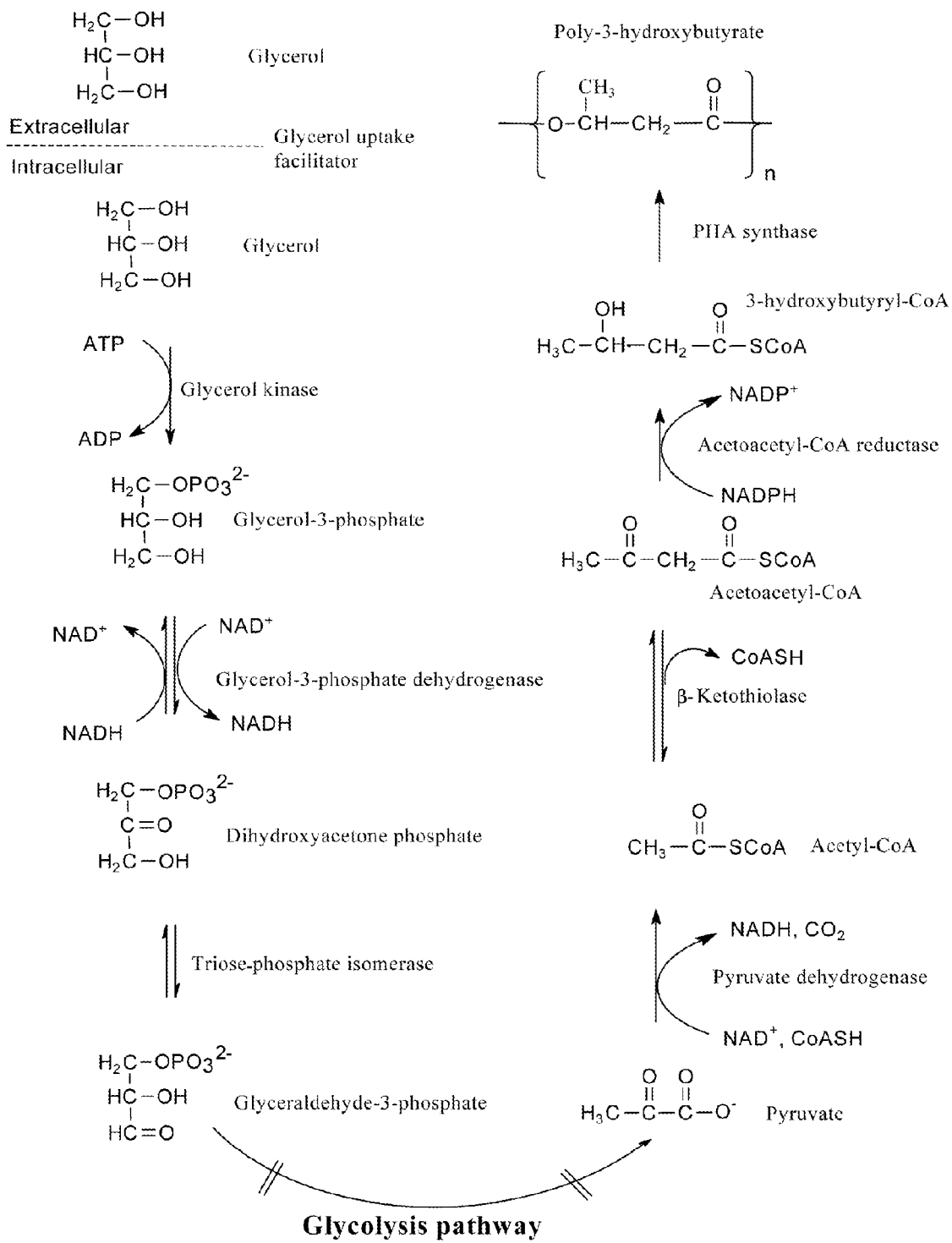
FIG. 1. Pathway for glycerol metabolism and PHA biosynthesis.

Methods are provided for producing biodegradable polyhydroxyalkanoates (PHAs) with desired geometry, molecular mass, mechanical and/or physical-chemical properties from glycerol, an inexpensive carbon source and byproduct of the biodiesel industry. Microorganisms capable of converting carbon to PHA can be used to convert biodiesel-glycerol to poly-3-hydroxybutyrate (PHB) or other monomer or copolymer PHAs via fermentation. The microorganisms are cultured in a medium comprises glycerol as primary carbon source, and at least one low molecular mass organic acid, for example, levulinic acid, propionic acid, valeric acid, dodecanoic acid, decanoic acid, octanoic acid, oleic acid and/or oleate, as a secondary carbon source. Biomass can be harvested from the culture medium and crude PHA extracted and purified, thereby recovering purified PHA with the desired property. After PHA isolation, a nucleating agent can be added to improve certain physical-chemical properties of the PHA, e.g., crystallization temperature, to enhance performance of the PHA during injection molding.

PHAs are a class of biodegradable polymers that have physical-chemical characteristics most closely related to polypropylene. PHAs are linear polyesters produced in nature by bacterial fermentation of sugar or lipids. It is well known in the art that over 100 different monomers can be combined within this family to give materials with varying properties, e.g., thermoplastic, elastomeric, etc., with melting-points ranging from 40-180° C. These biodegradable PHAs can be used as substitutes for petroleum-derived plastics such as polypropylene.

In one embodiment of the method, glycerol, which can be obtained as a byproduct of the biodiesel production process, is used as a primary carbon source for fermentation by a bacterium to produce PHAs.

In another embodiment, xylose, which can be obtained from wood hydrolysate, is used, instead of glycerol, as a primary carbon source for fermentation by a bacterium to produce PHAs.

In yet another embodiment, a combination of glycerol and xylose is used as the primary carbon source.

In another embodiment, a secondary carbon source is added during fermentation. Any secondary carbon source known in the art can be used.

In a specific embodiment, levulinic acid can be added as a secondary carbon source and a copolymer PHA can be synthesized that comprises both butyric acid and/or valeric acid, including but not limited to poly-3-hydroxybutyrate (PHB), poly-3-hydroxyvalerate (PHV), copolymer PHB-co-hydroxyvalerate (PHB-co-HV), and copolymer poly-3-hydroxybutyrate-co-poly-3-hydroxyvalerate (PHB-co-PHV). In other embodiments, other secondary carbon sources known in the art can be substituted for the levulinic acid to produce a PHB copolymer, e.g., PHB-co-3-hydroxypropionate (PHB-co-PHP) (Amin Cao, Ken-ichi Kasuya, Hideki Abe, Yoshiharu Doi and Yoshio Inoue. Studies on comonomer compositional distribution of the bacterial poly(3-hydroxybutyric acid-co-3-hydroxypropionic acid)s and crystal and thermal characteristics of their fractionated component copolyesters. Polymer, 1998, 39 (20): 4801-4816); PHB-co-PLA (Taek Ho Yang, Tae Wan Kim, Hye Ok Kang, Sang-Hyun Lee, Eun Jeong Lee, Sung-Chul Lim, Sun Ok Oh, Ae-Jin Song, Si Jae Park, Sang Yup Lee. Biosynthesis of polylactic acid and its copolymers using evolved propionate CoA transferase and PHA synthase. Biotechnology and Bioengineering, 2010, 105 (1): 150-160); PHB-co-PMB (Tina Lütke-Eversloh, Klaus Bergander, Heinrich Luftmann, and Alexander Steinbüchel. Biosynthesis of Poly(3-hydroxybutyrate-co-3-mercaptobutyrate) as a Sulfur Analogue to Poly(3-hydroxybutyrate) (PHB). Biomacromolecules, 2001, 2 (3): 1061-1065); PHB-co-P4HB (Masao Kunioka, Akira Tamaki, Yoshiharu Doi. Crystalline and thermal properties of bacterial copolyesters: poly(3-hydroxybutyrate-co-3-hydroxyvalerate) and poly(3-hydroxybutyrate-co-4-hydroxybutyrate). Macromolecules, 1989, 22 (2): 694C697); and PHB-co-PH4MV (Nuttapol Tanadchangsaeng, Asahi Kitagawa, Tetsuya Yamamoto, Hideki Abe and Takeharu Tsuge. Identification, Biosynthesis, and Characterization of Polyhydroxyalkanoate Copolymer Consisting of 3-Hydroxybutyrate and 3-Hydroxy-4-methylvalerate. Biomacromolecules, 2009, 10 (10): 2866C2874).

An advantage of the method provided by the invention is that it uses a byproduct of the biodiesel industry, glycerol, as the feedstock or starting material for producing biodegradable polymers as substitutes for petroleum-derived plastics such as polypropylene. Another advantage is that addition of levulinic acid as a secondary carbon source results in the incorporation of valeric acid into the PHA, which makes the resulting plastic more flexible as well as less brittle, and thereby increases the range of applications for the PHA. Another advantage is that the combination of a copolymer (with approximately 30 mole percent valeric acid) and 1-5% talc as a nucleating agent results in a more favorable crystallization temperature for producing biodegradable plastics by injection molding.

For clarity of disclosure, and not by way of limitation, the detailed description of the invention is divided into the subsections set forth below.

Microorganisms

Methods are provided for producing polyhydroxyalkanoates (PHAs) using biodiesel-glycerol, an inexpensive carbon source and byproduct of the biodiesel industry. Bacterial fermentation can be used to convert glycerol to PHAs.

Any strain of bacteria known in the art that produces PHAs can be used for producing PHAs according to the methods of the invention. Such microorganisms can include, but are not limited to: *Burkholderia* (formerly *Pseudomonas*) *cepacia, Ralstonia eutropha, Alcaligenes latus, Paracoccus denitrificans, Cupriavidus necator, Methylobacterium rhodesianum*, and various species of *Pseudomonas* such as *Pseudomonas corrugata, Pseudomonas oleovorans* and *Pseudomonas putida* (Choi J I, Lee S Y. Process analysis and economic evaluation for poly(3-hydroxybutyrate) production by fermentation. *Bioprocess Eng.* 1997; 17:335-342; Ren Q, De Roo G, Van Beilen J B, Zinn M, Kessler B, Witholt B. Poly (3-hydroxy-alkanoate) polymerase synthesis and in vitro activity in recombinant *Escherichia coli* and *Pseudomonas putida*. *Appl Microbiol Biotechnol.* 2005; 69:286-292; Slater S, Houmiel K L, Tran M, Mitsky T A, Taylor N B, Padgette S R, Gruys K J. Multiple β-ketothiolases mediate poly(β-hydroxyalkanoate) copolymer synthesis in *Ralstonia eutropha*. *J Bacteriol.* 1998; 180:1979-1987; Tsuge T, Fukui T, Matsusaki H, Taguchi S, Kobayashi G, Ishizaki A, Doi Y. Molecular cloning of two (R)-specific enoyl-CoA hydratase genes from *Pseudomonas aeruginosa* and their use for polyhydroxyalkanoate synthesis. *FEMS Microbiol Lett.* 1999; 184: 193-198). These microorganisms have been shown to produce various polyesters with different subunits (Steinbuchel A, Valentin H E. Diversity of bacterial polyhydroxyalkanoic acids. *FEMS Microbiol Lett.* 1995; 128:219-228).

In another embodiment, recombinantly engineered bacterial strains can be used for fermentation. Such engineered strains can be used to modulate the ratio of polymers in a copolymer PHA, e.g., hydroxybutyrate: hydroxyvalerate (HB:HV).

Methods for modulating the ratio of polymers in copolymer PHAs using engineered strains are known in the art. For example, Aldor and Keasling (2001, Metabolic engineering of poly(3-hydroxybutyrate-co-3-hydroxyvalerate) composition in recombinant *Salmonella enterica* serovar *typhimurium*, Biotechnology and Bioengineering 76(2):108-14) discloses that the composition of P(3HB-co-3HV) can be controlled by metabolic engineering of a recombinant *Salmonella enterica* strain, which involves "dialing the composition" by varying the induction level of a critical PHA biosynthetic gene. These methods can be readily adapted by the skilled practitioner to methods of producing other copolymer PHAs using PHA-producing microorganisms.

Schubert et al. (1998, Cloning of the *Alcaligenes eutrophus* poly-β-hydroxybutyrate synthetic pathway and synthesis of PHB in *Escherichia coli*. J. Bacteriol. 170, 5837-5847) discloses methods for producing PHA expression in *E. coli* transformed with constitutively expressed PHA biosynthesis genes of *R. eutropha*.

Choi et al. (1998, Cloning of the *Alcaligenes latus* polyhydroxyalkanoate biosynthesis genes and use of these genes for enhanced production of poly(3-hydroxybutyrate) in *Escherichia coli*, Appl. Environ. Microbiol. 64, 4897-4903) discloses methods for cloning PHA biosynthesis genes from *Alcaligenes latus*. See, also, e.g., U.S. Pat. No. 6,593,116 (Huisman et al., Jul. 15, 2003, Transgenic microbial polyhydroxyalkanoate producers) and U.S. Pat. No. 6,316,262 (Huisman et al., Nov. 13, 2001, Biological systems for manufacture of polyhydroxyalkanoate polymers containing 4-hydroxyacids).

Derivatized PHA homopolymers, copolymers, terpolymers, etc., can be produced by selecting fermenting microorganisms equipped with the metabolic machinery for utilization of the appropriate precursor PHA substrates. In one embodiment, this can be accomplished by genetically engineering microorganisms using methods known in the art to express required metabolic genes. In another embodiment, this can be accomplished by pre-fermentative enzymatic treatment of PHA substrates for the production of novel polymers with unique backbone and side-chain structures. The resulting polymers can display unique physical, chemical, and mechanical properties, related to their monomeric compositions and crystalline structures.

Culture of Microorganisms and Methods for Producing Polyhydroxyalkanoates (PHAs)

Standard methods known in the art for laboratory (small-scale) culture or industrial (large-scale) fermentation can be used to culture bacteria to produce PHAs. For pilot plant-scale fermentation, a commercially available fermentor (e.g., 400-L fermentor Model No: IF 400, New Brunswick Scientific Co., Inc. New Brunswick, N.J.) can be used. A fed-batch method can be used and low-grade purity glycerol (50-85% purity) can be added as the primary carbon source.

In one embodiment, a PHA producing bacterium such as *Burkholderia cepacia* ATCC 17759 can be cultured using standard small- or large-scale methods of fermentation. A nitrogen-limited mineral salts medium can be used in the fermentation (e.g., Bertrand J L, Ramsay B A, Ramsay J A, Chavarie C. Biosynthesis of poly-beta-hydroxyalkanoates from pentoses by *Pseudomonas pseudoflava*. *Appl Environ Microbiol.* 1990; 56:3133-3138).

In one embodiment, the primary carbon source for the fermentation is glycerol, preferably in the range of 86-92% purity to produce a desired PHA having a desired geometry, molecular mass, mechanical and/or physical-chemical property, although higher % (more expensive) and lower % purities of glycerol can be used. The glycerol is preferably diluted to an initial concentration of 2%-5% in the medium.

In one embodiment, at 24 h or 48 h of fermentation, the primary carbon source, e.g., glycerol, can be added to the medium (e.g., at a concentration of 2%-5% of the medium), and cultures can be harvested using standard techniques at 72 h.

In a specific embodiment, biodiesel-glycerol, i.e., glycerol that is produced during the biodiesel process, is used. Biodiesel-glycerol and methods for its production (e.g., as a byproduct of the biodiesel fuel production process) are well known in the art. Biodiesel-glycerol is usually not altered prior to being separated from biodiesel fuel and having methanol removed. Biodiesel-glycerol can be used directly in the bacterial fermentation to produce PHAs. Biodiesel-glycerol of lower purity can be used, but will produce lower yields of the desired PHA. Fermentation may also be partially inhibited when biodiesel-glycerol of lower purity is used, owing to methanol contamination of the biodiesel-glycerol. In one embodiment, biodiesel-glycerol at a concentration as low as 30-35% is used. In another embodiment, biodiesel-glycerol at a concentration as low as 34% is used In another embodiment, the primary carbon source is xylose, which can be used in the range of 5% to greater than 99% purity. Xylose is generally commercially available at greater than 99% purity. However, in another embodiment, the primary carbon source is the xylose that is present in a wood hydrolysate. The concentration of xylose in wood hydrolysate is typically in the range of 5-15% due to the presence of other organic compounds.

In certain embodiments, both xylose and glycerol are used as primary carbon sources in the culture medium. Xylose (preferably 50-85% purity) can be added at a concentration of 2-5% into the medium. Preferably, methanol has been removed or reduced below 0.05% in the primary carbon source(s).

When using glycerol or biodiesel-glycerol as the carbon source, the concentration of glycerol is preferably strictly controlled. By regulating the glycerol content, different molecular masses of PHB or PHA can be produced to meet the diverse criteria of various industrial and medical applications. For example, Keenan et al. (Keenan T M, Tanenbaum S W, Stipanovic A J, Nakas J P. Production and characterization of poly-beta-hydroxyalkanoate copolymers from *Burkholderia cepacia* utilizing xylose and levulinic acid. *Biotechnol Prog.* 2004; 20:1697-1704) disclose methods for regulating the compositional content of PHB-co-PHV using xylose and levulinic acid. Using this method, glycerol and levulinic acid can be used to regulate compositional content. In certain embodiments, control or modulation of the concentration of levulinic acid can be used to regulate the composition of the co-polymer, for example, from 0 mole percent 3-OH-valeric acid to greater than 60 mole percent 3-OH-valeric acid.

In one embodiment, PHAs, e.g., poly-3-hydroxybutyric acid or a PHA of similar structure and size (i.e., a short or medium chain-length monomer) may be end-capped with glycerol as disclosed herein, i.e., a terminal carboxyl group reacting with the hydroxyl groups of glycerol. PHA chains end-capped with glycerol are generated during fermentation in the presence of glycerol by the fermenting organism, i.e., as the PHA chains are synthesized they are end-capped by the fermenting organism.

Glycerol and xylose concentrations can be measured using standard methods. For example, to measure glycerol concentration, the Free Glycerol Reagent kit can be used (Cat. F6428, Sigma, St. Louis, Mo.). Using this test kit, the reactions are incubated for 5 min at 37° C. and the absorbances recorded spectrophotometrically at 540 nm using a commercially available spectrophotometer (e.g., CARY 300 Spectrophotometer, Varian Inc. USA) as described per the instructions of the manufacturer.

In another embodiment, a secondary carbon source is added during fermentation. In a specific embodiment, levulinic acid can be added as a secondary carbon source and a copolymer PHA can be synthesized that comprises both butyric acid and valeric acid, including but not limited to poly-3-hydroxybutyrate (PHB), PHV (poly-3-hydroxyvalerate), and copolymer poly-3-hydroxybutyrate-co-poly-3-hydroxyvalerate (PHB-co-PHV). In other embodiments, other secondary carbon sources known in the art can be substituted for the levulinic acid to produce a PHB copolymer.

PHAs that can be produced using the methods of the invention can have varying monomers and include but are not limited to: poly-3-hydroxybutyrate (PHB); poly-3-hydroxy- valerate (PHV); poly-3-hydroxypropionate (PHP); poly lactic acid (PLA); poly-3-mercaptobutyrate (PMB); poly-4-hydroxybutyrate (P4HB); poly-3-hydroxy-4-methylvalerate (PH4MV); and poly-4-hydroxyvalerate (P4HV). The most common short-chain-length PHAs consist of PHB, PHV, PHB-co-PHV. When different co-substrates (the secondary carbon sources) are provided for PHA biosynthesis using *Burkholderia cepacia* or other microorganisms, novel monomers may be incorporated and form new copolymers and terpolymers, such as PHB-co-PHP, PHB-co-PLA, PHB-co-PMB, PHB-co-P4HB, PHB-co-PH4MV, PHB-co-PHV-co-P4HV. PHAs with different and varying ratios of monomers exhibit different mechanical properties, which allows for a broad range of pharmaceutical and medical applications.

In one embodiment, a PHA that is produced with a desired geometry, molecular mass, mechanical and/or physical-chemical property is a PHA copolymer of a plurality of different PHA polymers in a desired ratio, and the ratio of glycerol (primary carbon source) to the secondary carbon source in the culture medium is predetermined (or determined to be sufficient), using methods known in the art, to produce the desired ratio of PHA polymers in the PHA copolymer. By controlling the concentrations of the primary and secondary carbon sources, a PHA co-polymer (i.e., a PHA with two different subunits) can be produced with different proportions of the two subunits.

In another embodiment, the PHA with the desired geometry, molecular mass, mechanical and/or physical-chemical property is a PHA copolymer of butyric acid and valeric acid in a desired ratio, the secondary carbon source is levulinic acid, and the ratio of glycerol to levulinic acid in the culture medium is predetermined (or sufficient) to produce the desired ratio of butyric acid and valeric acid in the PHA copolymer.

In another embodiment, fatty acid substrates longer than levulinic acid are used as secondary carbon sources and are added to the fermentation medium to produce polymers that comprise medium-chain length PHA (MCL-PHA) monomers in addition to the 3-HV and 3-HB monomers. Such MCL-PHA monomers include, e.g., 3-hydroxyhexanoate (3-HHx) and 3-hydroxyoctanoate (3-HO). Fatty acids that are included as additional carbon sources include, e.g., dodecanoic acid, decanoic acid and octanoic acid, as well as longer chain fatty acids such as oleic acid or oleate. Inclusion of such additional carbon sources can result in novel polymers with more desirable desired geometry, molecular mass, mechanical and/or physical-chemical properties (e.g. lower melting points, greater flexibility, greater elongation to break percentages, etc.). A desired mechanical property can be, e.g., increased elongation-to-break or resistance to breaking. A desired physical-chemical property can be, e.g., increased crystallization temperature.

In a specific embodiment, a method is provided for producing polyhydroxyalkanoate (PHA) with a desired geometry, molecular mass, mechanical and/or physical-chemical property by microbial fermentation, the method comprising the steps of:
  (a) providing a culture medium, wherein the culture medium comprises: glycerol as primary carbon source, and at least one low molecular mass organic acid as a secondary carbon source;
  (b) culturing a microorganism that converts carbon to PHA in the culture medium;
  (c) harvesting biomass from the culture medium;
  (d) extracting crude PHA from the harvested biomass; and
  (e) purifying PHA from the crude PHA, thereby recovering purified PHA with the desired geometry, molecular mass, mechanical and/or physical-chemical property. The low molecular mass organic acid can include, but is not limited to, levulinic acid, propionic acid, valeric acid, dodecanoic acid, decanoic acid, octanoic acid, oleic acid and oleate.

In a specific embodiment, the microorganism can be grown first on a medium comprising xylose and then switched to a medium comprising glycerol. For example, in a specific embodiment, longer chains of PHAs can be produced from xylose and then end-capped with glycerol. If grown on glycerol from start to finish, the PHAs will be shorter and end-capped with glycerol.

In another embodiment, a method is provided for producing a desired geometry, molecular mass, mechanical and/or physical-chemical property in a PHA polymer comprising the steps of:

(a) providing a culture medium, wherein the culture medium comprises a non-glycerol carbon source, e.g., xylose, galactose, glucose, etc., as primary carbon source;

(b) culturing a microorganism that converts carbon to PHA in the culture medium to produce PHA polymer chains;

(c) adding glycerol to the culture medium in an amount sufficient to end-cap the PHA polymer chains to produce the desired geometry, molecular mass, mechanical and/or physical-chemical property in the end-capped PHA polymer;

(d) further culturing the microorganism in the culture medium with added glycerol to produce the desired geometry, molecular mass, mechanical and/or physical-chemical property in the end-capped PHA polymer;

(e) harvesting biomass from the culture medium;

(f) extracting crude PHA from the harvested biomass; and (g) purifying PHA from the crude PHA, thereby recovering end-capped PHA polymer having the desired geometry, molecular mass, mechanical and/or physical-chemical property.

Suitable non-glycerol carbon sources for producing PHAs are known in the art, e.g., xylose, galactose and glucose, to name but a few.

Thus in various embodiments, xylose can be omitted from the culture medium and the microorganism can be cultured in a medium comprising glycerol as primary carbon source. Alternatively, the microorganism can be grown on xylose, galactose, glucose, or another carbon source known in the art, and glycerol added during a subsequent time during fermentation; the microorganism will still end-cap the resulting polymers with glycerol.

In another embodiment, after purifying PHA from crude PHA, a nucleating agent (e.g., talc) can be added to the purified PHA in an amount sufficient to generate the desired geometry, molecular mass, mechanical and/or physical-chemical property in the purified PHA. Appropriate nucleating agents and sufficient amounts of such agents can be easily determined using methods known in the art.

In a specific embodiment, the nucleating agent is added at a desired concentration to improve certain physical-chemical characteristics, especially crystallization temperature, to enhance performance of the PHA polymers during injection molding.

In another embodiment, a method is provided for producing poly-hydroxybutyric acid (PHB) comprising the steps of:

(a) providing a culture medium, wherein the culture medium comprises glycerol as primary carbon source, (b) culturing a microorganism that converts carbon to PHA in the culture medium;

(c) harvesting biomass from the culture medium;

(d) extracting crude PHA from the harvested biomass; and (e) purifying PHA from the crude PHA.

A method is also provided for producing a desired geometry, molecular mass, mechanical and/or physical-chemical property in a PHA polymer comprising the steps of:

(a) providing a culture medium, wherein the culture medium comprises glycerol as primary carbon source;

(b) culturing a microorganism that converts carbon to PHA in the culture medium to produce end-capped PHA polymer chains having the desired geometry, molecular mass, mechanical and/or physical-chemical property;

(c) harvesting biomass from the culture medium;

(d) extracting crude PHA from the harvested biomass; and (e) purifying PHA from the crude PHA, thereby recovering end-capped PHA polymer having the desired geometry, molecular mass, mechanical and/or physical-chemical property.

In certain embodiments, during the fermentation, non-end capped PHA polymer chains can be produced in a non-glycerol containing medium, and their end-capping can be subsequently initiated or regulated during fermentation by addition of glycerol.

For example, end-capped polymers are only generated when the organism is grown in a medium with glycerol as the major carbon source. The PHAs produced (e.g., entirely PHB if only glycerol is the carbon source) will be end-capped so that polymers of 3-hydroxybutyric acid are produced with a glycerol moiety on the end. If one begins with another carbon source, e.g. xylose, and later adds in glycerol, the organism will make normal PHAs but will end-cap them with glycerol.

Biomass and PHA Isolation

Standard methods known in the art can be used to harvest the PHAs produced. For example, the methods of Keenan et al. (Keenan, T. M., S. W. Tanenbaum, A. J. Stipanovic, and J. P. Nakas. 2004. Production and characterization of poly-β-hydroxyalkanoate copolymers from *Burkholderia cepacia* grown on xylose and levulinic acid. Biotechnol. Prog. 20: 1697-1704), Kessler et al. (B. Kessler, R. Weusthuis, B. Witholt, G. Eggink. 2001. Production of Microbial Polyesters: Fermentation and Downstream Processes. Advances in Biochemical Engineering/Biotechnology, 71: 159-182), Jacquel et al. (Nicolas Jacquel, Chi-Wei Lo, Yu-Hong Wei, Ho-Shing Wu and Shaw S. Wang. 2008. Isolation and purification of bacterial poly(3-hydroxyalkanoates). Biochemical Engineering Journal, 39: 15-27) or Yu et al. (Jian Yu, Lilian X. L. Chen. 2006. Cost-Effective Recovery and Purification of Polyhydroxyalkanoates by Selective Dissolution of Cell Mass. Biotechnology Progress, 2006, 22: 547-553) can be used.

Cultures can be harvested from bench-scale fermentations by centrifuging the broth using standard centrifugation methods (e.g., at 7000×g for 10 min). The harvested biomass is then subsequently washed with $H_2O$ (e.g., tap, deionized or distilled) and centrifuged again to remove the supernatant and frozen under standard conditions (e.g., at −20° C.) until lyophilization.

Cultures can be harvested from industrial-scale fermentation by centrifuging the broth using standard centrifugation methods (e.g., at 16,000 rpm) using a continuous flow centrifuge). The harvested biomass is then frozen under standard conditions and lyophilized (e.g., at −80° C. and 200 militorr) for 24 h. The dry biomass can be then be ground to a powder, mixed with chloroform (10 ml chloroform/1 g dry biomass) and stirred at room temperature for 24 h.

For the extraction and purification of bench-scale quantities of PHA, methods known in the art can be used (e.g., Keenan T M, Tanenbaum S W, Stipanovic A J, Nakas J P. Production and characterization of poly-beta-hydroxyalkanoate copolymers from *Burkholderia cepacia* utilizing xylose and levulinic acid. *Biotechnol Prog.* 2004; 20:1697-1704).

For the extraction and purification of industrial-scale quantities of PHA, methods known in the art can be used. For example, lyophilized cell mass (e.g., 1 kg) can be stirred in chloroform (e.g., 9 l) at room temperature for 24 h. The polymer solution can be concentrated by standard methods, e.g., rotary evaporation at 70° C. A standard distillation system can be used to recover chloroform. The polymer is precipitated from this solution using standard methods. For example, the PHA solution can be added to cold methanol, e.g., 1 vol PHA solution/5 vol methanol. The fiber-shaped polymers can be collected and washed with additional methanol.

The PHA can be extracted and purified using methods known in the art. For example, the methods of Naylor et al., U.S. Pat. No. 5,871,980 ("Process for the microbiological production of PHA-polymers") can be used for extraction and purification of industrial-scale quantities of PHA.

The hydroxyl-containing functionalities of the unpolymerized 3-hydroxybutyrate and 3-hydroxyvalerate monomers are potentially oxidizable substrates that can, in certain embodiments be condensed with other moieties to produce derivatized monomers and thus drastically different crystalline lattice structures in the resultant PHA polymers (changing physical, chemical, and mechanical properties).

For example, such moieties can include, but are not limited to carboxylic acids, amines, amides, esters, halogens, alkyl groups, acyl chlorides, acid anhydrides, carboxylate esters, sulfonates, tosylates, phosphite esters, and chlorosulfates.

The oxidation or derivatization reactions can be catalyzed by a selected enzyme prior to addition to the fermentation medium. Such enzymes and their selection are known in the art. Typically, the oxidation or condensation (e.g., to another molecule that offers unique structural features) will occur at the 3-OH position. Co-substrate derivatives, such as derivatives of levulinic acid, propionic acid, and valeric acid containing aromatic residues, can be added to the PHA fermentation as the co-substrate with xylose, to then be recognized and acted upon by native or recombinant monomer-supplying enzymes and PHA polymerase enzymes. For example, oxidation at the 3-hydroxy position of the PHA precursor, 3-OH-valeryl-CoA, can produce unique monomers that would be recognized by the host strain's PHA synthase/polymerase and incorporated into the growing PHA chain(s). Thus, in some embodiments, oxidized or otherwise derivatized co-substrates can be used. Such derivatized carbon sources are typically prepared outside the fermentation and added to the fermentation medium, although genetic engineering techniques known in the art permit the introduction of genes into the fermenting microorganism that are necessary to derivatize the carbon source biologically and in situ.

In one embodiment, PHAs are produced with 4-HV monomers. Steinbuchel et al. (Steinbuchel, A., G. Schmack, V. Gorenflo. 1998. Biotechnological production and characterization of polyesters containing 4-hydroxyvaleric acid and medium-chain-length-hydroxyalkanoic acids. Macromolecules 31:644-649) demonstrated the production of PHA polyesters composed of 3HB, 3HV, 4HV, and medium-chain length hydroxyalkanoate monomers (hexanoate and octanoate), utilizing a recombinant strain of *Pseudomonas putida*. The controlled fermentation used octanoic and levulinic acids as carbon sources. This study purposely used levulinic acid as a precursor to 4-HV, because 4-hydroxyvaleric acid is not commercially available. By proper selection of the fermenting microorganism, e.g., by genetic engineering using art-known methods, or by appropriate selection of fermentation conditions, polymers can be produced comprising 4-HV monomers through use of glycerol and levulinic acid as the carbon sources.

Addition of Nucleating Agent to Purified PHAs to Improve their Physical-Chemical Characteristics In another embodiment, after harvesting the bacteria and extracting the PHAs, a nucleating agent such as talc can be added at various concentrations, e.g., 0.1-1%, 1-5%, 5%-10%, to improve certain physical-chemical characteristics, especially crystallization temperature, to enhance performance of PHAs during injection molding. A number of nucleating agents known in the art are suitable for this use, include HPN-68L (bicyclo[2.2.1]heptane-2,3-dicarboxylic acid, disodium salt), and ULTRATALC®609 (magnesium silicate hydrate (60% $SiO_2$, 32% MgO)).

In a specific embodiment, a PHA copolymer comprising approximately 30 mole percent valeric acid is combined with 1-5% talc as a nucleating agent to produce a PHA with a more favorable crystallization temperature for injection molding. Example 6.2 demonstrates this improvement of crystallization temperature.

By adding talc, the crystallization temperature can be increased significantly, i.e. approximately 15-20° C. for a homopolymer (e.g., polyhydroxybutyric acid) and approximately 25-40° C. for a copolymer (e.g., poly-hydroxybutyric acid-co-valeric acid). This is advantageous since it decreases the cooling time of PHAs in any injection molding process, thus saving time and money.

Polyhydroxyalkanoates (PHAs)

Art-known PHAs that can be produced by the methods of the invention include, but are not limited to: homopolymer poly-3-hydroxybutyrate (PHB), PHV (poly-3-hydroxyvalerate), and copolymer poly-3-hydroxybutyrate-co-poly-3-hydroxyvalerate (PHB-co-PHV). By incorporating PHV with PHB to form the copolymer, lower crystallinity and better elongation can be obtained which exhibit more desirable mechanical properties (Keenan T M, Tanenbaum S W, Stipanovic A J, Nakas J P. Production and characterization of poly-beta-hydroxyalkanoate copolymers from *Burkholderia cepacia* utilizing xylose and levulinic acid. *Biotechnol Prog.* 2004; 20:1697-1704).

Figure 2:
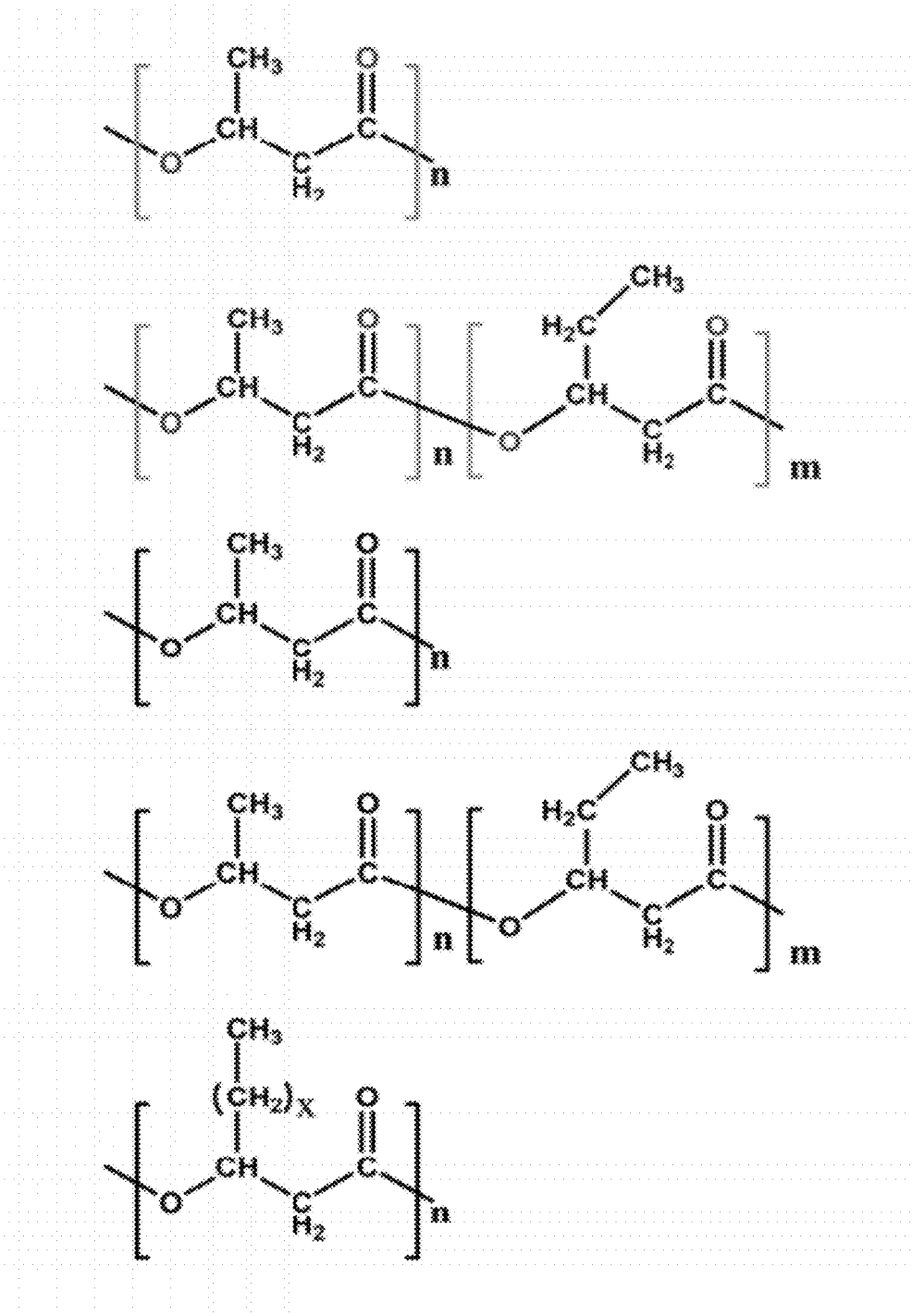
FIG. 2. Row 1: Structural diagram for polyhydroxybutyric acid (PHB) where the only monomer present is butyric acid. Row 2: the copolymer pHB-coHV, i.e., a polymer consisting of butyric acid and valeric acid). Rows 3-5: general formulae for medium chain length polymers.

FIG. 1 summarizes the art-known biosynthetic pathway for glycerol metabolism and PHA biosynthesis. FIG. 2 shows in Row 1, a structural diagram for polyhydroxybutyric acid (PHB) where the only monomer present is butyric acid; in Row 2, the copolymer pHB-coHV, i.e., a polymer consisting of butyric acid and valeric acid). The general formula for medium chain-length polymers is shown in Row 3 where X refers to a chain length of two to six carbons.

PHAs produced by the methods of the invention can be analyzed using analytic methods known in the art, e.g., gas chromatography (GC), molecular mass determination, thermal analysis, and nuclear magnetic resonance (NMR).

The following example is offered by way of illustration and not by way of limitation.

EXAMPLES

Example 1

Production and Characterization of Poly-3-Hydroxybutyrate from Biodiesel-Glycerol by *Burkholderia cepacia* ATCC 17759

Introduction

In this example, glycerol, a byproduct of the biodiesel industry, is used by bacteria as an inexpensive carbon source for the production of value-added biodegradable polyhydroxyalkanoates (PHAs). To examine alternative uses for low-value biodiesel waste glycerol, small scale fermentations were initially performed by *B. cepacia* in shake flasks and analyzed for PHB production using glycerol as a carbon source. Physical-chemical properties of PHB produced by *B. cepacia* grown on reagent-grade glycerol were determined and it was established that the molecular mass decreased when glycerol was used as a carbon source. Subsequently, *B. cepacia* was used to convert biodiesel-glycerol to PHB via fermentation at a pilot plant (200-L) scale.

*Burkholderia cepacia* ATCC 17759 synthesized poly-3-hydroxybutyrate (PHB) from glycerol concentrations ranging from 3% to 9% (v/v). Increasing the glycerol concentration resulted in a gradual reduction of biomass, PHA yield and molecular mass ($M_n$ and $M_w$) of PHB. The molecular mass of PHB produced utilizing xylose as a carbon source was also decreased by the addition of glycerol as a secondary carbon source dependent upon the time and concentration of the addition. $^1$H-NMR revealed that molecular masses decreased due to the esterification of glycerol with PHB resulting in chain termination (end capping). However, melting temperature and glass transition temperature of the end-capped polymers showed no significant difference when compared to the xylose-based PHB. The fermentation was successfully scaled up to 200 L for PHB production and the yield of dry biomass and PHB were 23.6 g/L and 7.4 g/L, respectively.

Materials and Methods

Microorganism and Fermentation Conditions

*Burkholderia cepacia* ATCC 17759 was used in both shake flask as well as pilot scale (200-L) fermentations. The nitrogen-limited mineral salts medium used in the fermentations was initially described by Bertrand et al. (Bertrand J L, Ramsay B A, Ramsay J A, Chavarie C. Biosynthesis of poly-beta-hydroxyalkanoates from pentoses by *Pseudomonas pseudoflava*. *Appl Environ Microbiol.* 1990; 56:3133-3138). For shake-flask experiments, all cultures were shaken at 30° C. and 150 rpm and the concentration of nitrogen was further reduced to 1.5 g/L. Glycerol (99.5%, EMD, Gibbstown, N.J.) and xylose (99% purity, Acros, Waltham, Mass.) were used to produce PHB for physical-chemical characterizations and were autoclaved separately. All shake flask experiments were performed in 500 mL flasks (baffled) containing 100 mL of medium with metal enclosures.

In experiments using both xylose and glycerol as carbon sources, xylose (2.2%) was initially added into the medium. At 24 h or 48 h, 2% or 5% glycerol was added to the medium, and cultures were harvested at 72 h. Only 2.2% xylose was used as a carbon source for a control. When using the 400-L fermentor (Model No: IF 400, New Brunswick Scientific Co., Inc. Edison, N.J.), a fed-batch method was used and glycerol (85% purity) from a biodiesel-producing facility (Twin Rivers Technologies, Quincy, Mass.) was added as the primary carbon source.

Glycerol Content

Glycerol concentration was measured using the Free Glycerol Reagent kit (Cat. F6428, Sigma, St. Louis, Mo.). The reactions were incubated for 5 min at 37° C. and the absorbances were recorded spectrophotometrically at 540 nm (CARY 300 Spectrophotometer, Varian, Walnut Creek, Calif.) as described per the instructions of the manufacturer.

Biomass and PHA Isolation

Cultures were harvested from shake flasks by centrifugation at 7000×g for 10 min (Sorvall model SS-3, Thermo Fisher Scientific Inc., Waltham, Mass.). The biomass was subsequently washed with distilled $H_2O$ and centrifuged again to remove the supernatant and stored at −20° C. until lyophilization. For cultures grown in the 400-L fermentor, the broth was centrifuged at 16,000 rpm using a continuous flow centrifuge (CEPA High Speed Centrifuge Z81 G, New Brunswick Scientific, Edison, N.J.).

The harvested biomass was then frozen and lyophilized at −80° C. and 200 militorr for 24 h. The dry biomass was subsequently ground to a powder, mixed with chloroform (10 ml chloroform/1 g dry biomass) and stirred at room temperature for 24 h. For the extraction and purification of bench-scale quantities of PHA, the procedure of Keenan et al. (Keenan T M, Tanenbaum S W, Stipanovic A J, Nakas J P. Production and characterization of poly-beta-hydroxyalkanoate copolymers from *Burkholderia cepacia* utilizing xylose and levulinic acid. *Biotechnol Prog.* 2004; 20:1697-1704) was used for all biomass samples. For the purification of polymers from cells produced at the pilot-plant scale, lyophilized cell mass (1 kg) was stirred in 9 l of chloroform at room temperature for 24 h. The polymer solution was concentrated by rotary evaporation at 70° C. and a distillation system was used to recover chloroform. The polymer was precipitated from this solution via addition to cold methanol (1 vol PHA solution/5 vol methanol). Precipitated polymer samples exhibited a fibrous morphology and were washed with additional methanol.

Gas Chromatographic (GC) Analysis for PHAs

Monomer composition and yield of PHAs were determined by gas chromatography on a on a GC2010 equipped with AOC-20i autosampler (Shimadzu, Columbia, Md.) as described previously by Nomura et al. (Nomura C T, Taguchi K, Taguchi S, Doi Y. Coexpression of genetically engineered 3-ketoacyl-ACP synthase III (fabH) and polyhydroxyalkanoate synthase (phaC) genes leads to short-chain-length-medium-chain-length polyhydroxyalkanoate copolymer production from glucose in *Escherichia coli* JM109. *Appl Environ Microbiol.* 2004; 70: 999-1007). Briefly, 15 mg of dry biomass were weighed, mixed with 2 ml of $H_2SO_4$/methanol (15:85) and 2 ml chloroform, and incubated at 100° C. for 140 min to extract the polymer and subject it to a methanolysis reaction to form methyl ester monomers. The mixture was then cooled to room temperature and 1 ml of distilled water was added and the solution was vortexed for 1 min. The mixture was allowed to separate into an aqueous and an organic phase and the organic layer (0.5 ml) was removed, filtered (PTFE membrane, 0.22 μm), and mixed with 0.5 ml 0.1% caprylic acid in chloroform. The mixture was subjected to analysis by gas chromatography with a flame ionization detector (FID). Application of the sample was by split injection of 1 μL onto a 30-m RTX®-5 (5% diphenyl-95% dimethyl polysiloxane) column with a 0.25 mm ID (Restek, Bellefonte, Pa.). The injection port was held at 280° C. and the oven housing the column was held at 100° C. for 3 min. The oven temperature was then raised 8° C. min$^{-1}$ to 280° C. where the column was held for 2 min. The oven temperature was raised to 310° C. at a rate of 20° C. min$^{-1}$ and held for 10 min to remove any residuals from the column before the next sample was applied. Products were detected by FID at a temperature of 310° C.

Molecular Mass Determination

Number average molecular weight ($M_n$) and weight average molecular weight ($M_w$) were determined by gel permeation chromatography (GPC) using an LC-20AD Liquid Chromatograph equipped with a SIL-20A auto-sampler and RID-10A refractive index detector (Shimadzu, Columbia, Md.). PHB polymers were dissolved in chloroform to a final concentration of 0.7 mg/ml and filtered (PTFE membrane, 0.22 μm) before analysis. A Styrene divinylbenzene (SDV) 8×300 mm column with 5 μm porosity was used as the stationary phase (Polymer Standards Service, Warwick R.I.) with an oven temperature of 40° C. The mobile phase was chloroform at a flow rate of 1 ml/min.

Standard curves for molecular weight were created using polystyrene standards with a range from 682 to 1,670,000 Da and low polydispersities (Polystyrene High Mw Standards Kit, Polymer Standards Service, Warwick R.I.).

Thermal Analysis

Thermogravimetric analysis (Hi-Res TGA 2950, TA Instruments, New Castle, Del.) was used to determine the decomposition temperature ($T_{decomp.}$) of PHB. Ten milligrams of PHB film were folded into a platinum tray and subjected to a heating rate of 20° C./min from ambient to a final temperature of 500° C.

Differential scanning calorimetry (DSC, model 2920, TA Instruments) was used to characterize the melting temperature ($T_m$) and glass transition temperature ($T_g$) for all polymer samples. The temperature range for DSC varied from −50° C. to 250° C. at a heating rate of 10° C./min and a cooling rate of 5.0° C./min. Universal Analysis 2000 software was used for data analysis.

Nuclear Magnetic Resonance

End-capped PHB was analyzed by $^1$H NMR spectroscopy using a Bruker BioSpin AVANCE 600 (Bruker BioSpin Corporation, Billerica Mass.) operating at 600 MHz. Samples were prepared for analysis by dissolving solvent-cast film segments in deuterated chloroform [1% (w/v)] via mixing with mild heating. The analyses for glycerol and PHB were accomplished using XWIN-NMR version 3.1 software.

Results

Growth and PHB Yield of *B. cepacia*

Figure 3:
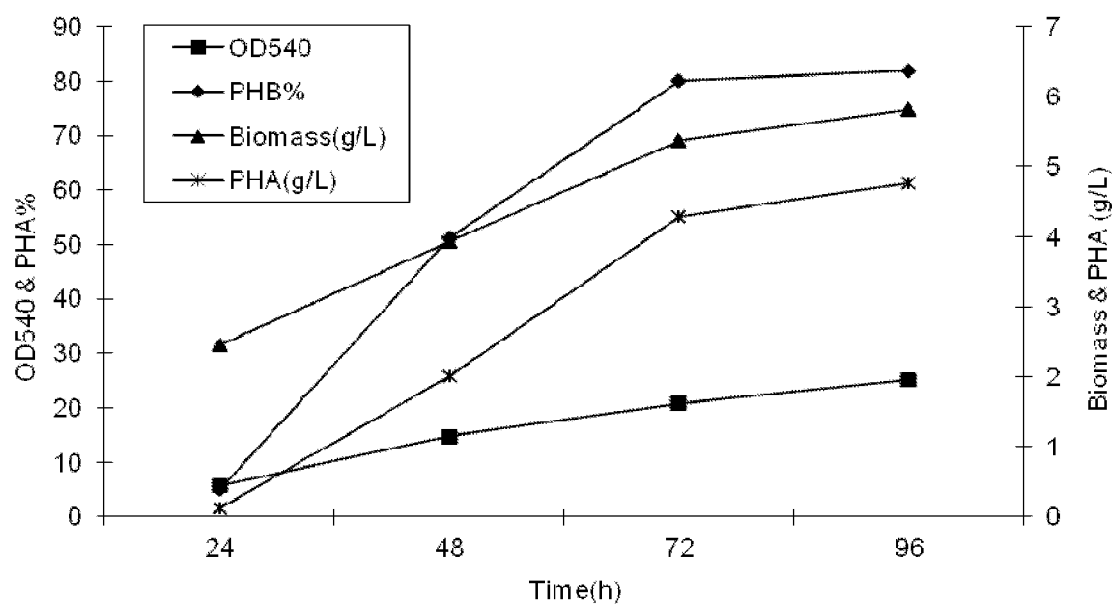
FIG. 3. Growth and PHA production by *B. cepacia* using 3% biodiesel-glycerol in shake flasks. X-axis, Time (h). Left Y-axis, OD540 & PHA %. Right Y-axis, Biomass & PHA (g/L). ■ OD540. ♦ PHA %. ▲ Biomass (g/L). * PHA (g/L).

In shake flask experiments, yields of dry biomass approached 5.8 g/L which was comprised of up to 81.9% PHB when using 3% (v/v) biodiesel-glycerol as the carbon source. This resulted in 4.8 g/L PHB production after 96 h shaking at 150 rpm and 30° C. (FIG. 3).

Figure 4:
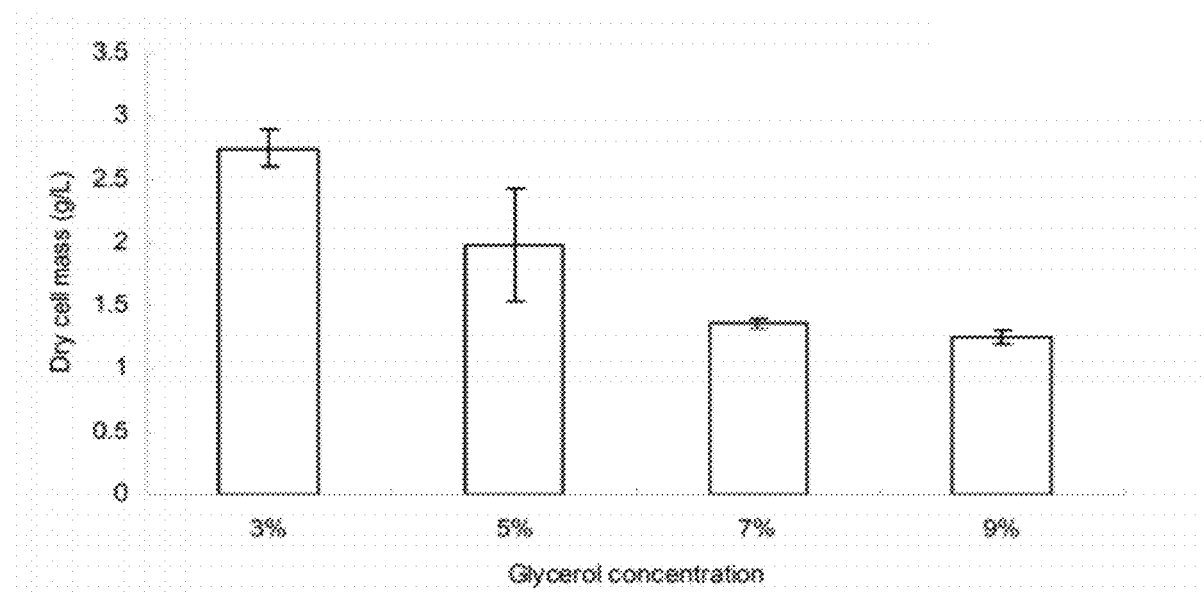
FIG. 4. Dry biomass of *B. cepacia* grown in shake flasks on different concentrations of pure glycerol. X-axis, Glycerol concentration. Y-axis, Dry cell mass (g/L).

When different concentrations of pure glycerol were added to the medium (FIG. 4), the glycerol content influenced the amount of final dry biomass. Specifically, higher concentrations of glycerol resulted in lower amounts of dry biomass. For example, dry biomass reached 2.8 g/L at 3% (v/v) glycerol added in shake flask experiments, whereas when 9% (v/v) glycerol was added, the amount of dry biomass decreased to 1.3 g/L.

Variation of Molecular Weights of PHB Produced from Glycerol in *B. cepacia*

Figure 5:
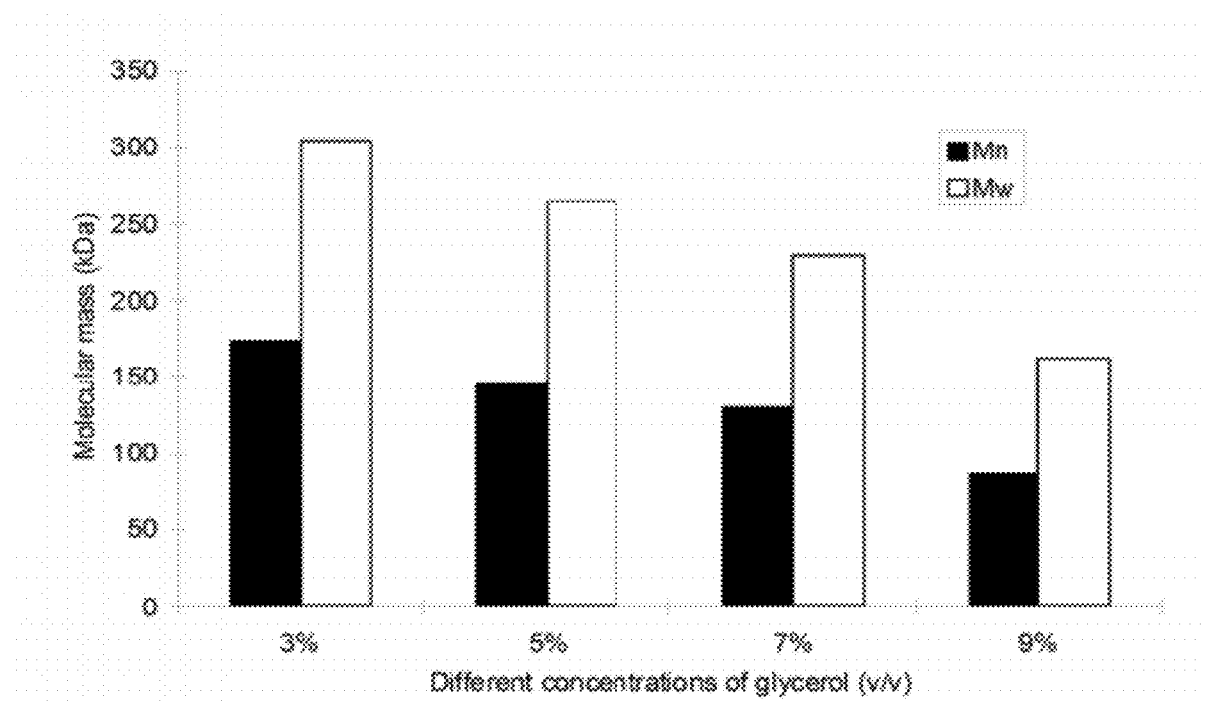
FIG. 5. Number-average molecular weight (Mn) and weight-average molecular weight (Mw) of PHB produced by *B. cepacia* grown with different concentrations of glycerol. X-axis, Different concentrations of glycerol (v/v). Y-axis, Molecular mass (kDa).

Number average molecular weights ($M_n$) and weight average molecular weights ($M_w$) of thin PHB solvent-cast films were determined by GPC. When concentrations of glycerol were increased from 3% to 9%, both $M_n$ and $M_w$ decreased gradually from 173 kDa and 304 kDa to 87 kDa and 162 kDa, respectively (FIG. 5).

Mixtures of xylose and glycerol were also examined as carbon sources. Initially, 2.2% (w/v) xylose was added to the cultures at the time of inoculation and glycerol was added at time points of 24 h and 48 h at concentrations of either 2% (v/v) or 5% (v/v). Subsequently, the cultures were harvested at 72 h. $M_n$ of PHB from 5% glycerol was lower than that from 2% glycerol added to the medium at the same time point. Higher glycerol concentrations resulted in the production of PHB with overall lower molecular mass (Table 1).

TABLE 1

Effect of concentrations and exposure times of glycerol on the number-average molecular weight (Mn) of PHB.

| Glycerol concentration (v/v) [a] | Exposure time in glycerol (h) [b] | | |
|---|---|---|---|
| | 0 | 24 | 48 |
| No glycerol (control) | 468.3 [c] | — | — |
| 2% | — | 174.6 | 133.6 |
| 5% | — | 138.4 | 114.0 |

[a] All treatments contained 2.2% (w/v) xylose as the primary carbon source.
[b] Glycerol additions were made at the time point of 24 and 48 h with all treatments harvested at 72 h.
[c] All data reported in kiloDalton (kDa).

Interestingly, when the cells were grown on the same concentration of glycerol (2% or 5%) with 2.2% xylose, PHB had lower $M_n$ (133.6 or 114.0 kDa) as cells were exposed to glycerol for a longer time period (48 h) and higher $M_n$ (174.6 or 138.4 kDa) when exposed to glycerol for a shorter time period (24 h), respectively. The same trend was observed for $M_w$ of PHB produced from 2% or 5% glycerol with 2.2% xylose (data not shown). When 2.2% xylose was provided as the sole carbon source, the $M_n$ reached 468.3 kDa (Table 1). The xylose-based PHB polymer was found to be of greater molecular mass than PHA produced from or exposed to glycerol. High concentrations of glycerol increased the opportunity for incorporation of glycerol into the polymer. Also, exposing the cells to glycerol for a longer time period increased the possibility to terminate the elongation of PHB. Therefore, higher concentrations of glycerol or longer exposure to glycerol resulted in PHB with lower molecular masses.

Figure 6:
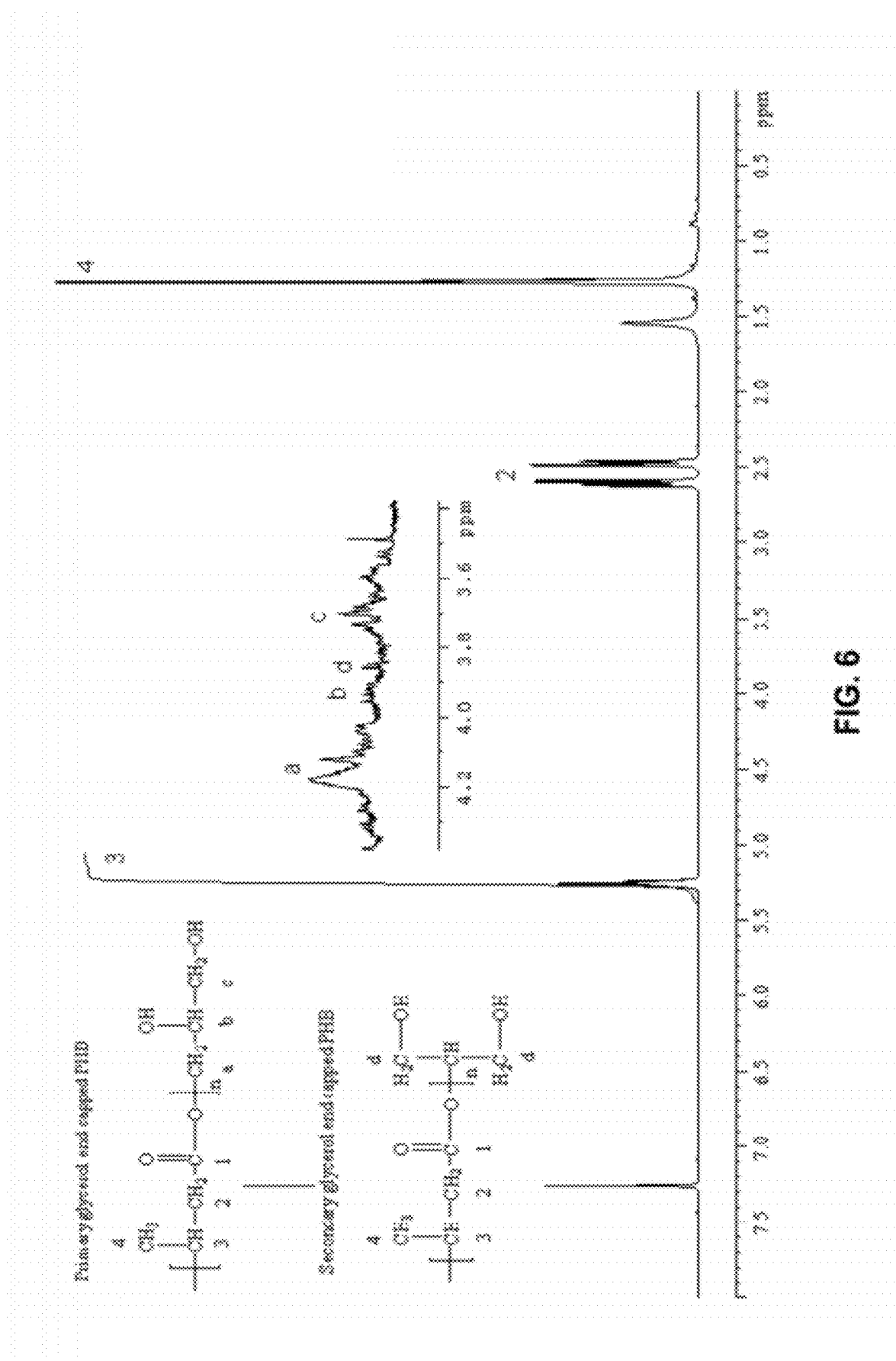
FIG. 6. $^1$H-NMR of PHB produced by *B. cepacia* grown on 7% glycerol as a carbon source. The expanded region indicates glycerol as the terminal end-group.

Characterization of PHB End-Capped with Glycerol by $^1$H NMR $^1$H NMR shows the results from PHB synthesized in the presence of 7% glycerol (FIG. 6). The full spectrum showed the expected resonances for PHB as demonstrated by the methyl group at 1.25 ppm, the methylene group between 2.45 and 2.65 ppm and the methine group at 5.25 ppm. However, expansion of the spectral region between 3.0 and 4.5 ppm revealed the presence of additional resonances corresponding to terminal glycerol groups. The expanded region with three resonances at 3.7 ppm, 3.95 ppm and 4.18 ppm showed the terminal esterification of glycerol to PHB through the primary hydroxyls ($C_1$ or $C_3$ positions of glycerol). Resonance at 3.86 ppm showed glycerol end-capping of PHB through the secondary hydroxyl group. Because glycerol is composed of 2 primary and 1 secondary hydroxyl groups, the possibility exists that the glycerol termination of PHB polymers could also be the result of covalent bonding at the secondary hydroxyl group of glycerol. These results were identical to those reported by Ashby et al. (Ashby R D, Solaiman D K, Foglia T A. Synthesis of short-/medium-chain-length poly (hydroxyalkanoate) blends by mixed culture fermentation of glycerol. *Biomacromolecules*. 2005; 6:2106-2112).

Mechanical Properties of PHB

Thermal characterization by DSC and TGA of PHB films is shown in Table 2.

TABLE 2

Physical-chemical properties of PHB produced from xylose or glycerol.

| PHB | $T_m$ (° C.) | $T_g$ (° C.) | $T_{decomp.}$ (° C.) |
|---|---|---|---|
| Xylose-based PHB [a] | 178.6 | −6.6 | 268.6 |
| Glycerol-based PHB [b] | 181.9 | 1.6 | 281.5 |

[a] PHB produced from 2.2% (w/v) xylose as sole carbon source.
[b] PHB produced from 3% (v/v) glycerol as sole carbon source.

Although the molecular mass of glycerol-based PHB was lower than that of xylose-based PHB, there was no significant change for both $T_g$ and $T_m$; however, $T_{decomp.}$ increased from 268.6° C. to 281.5° C. Higher decomposition temperature provides a broader separation between the required melting temperature for injection molding and thermal degradation of the polymers.

Pilot Scale (200-L) Fermentation Using Biodiesel-Glycerol

Figure 7:
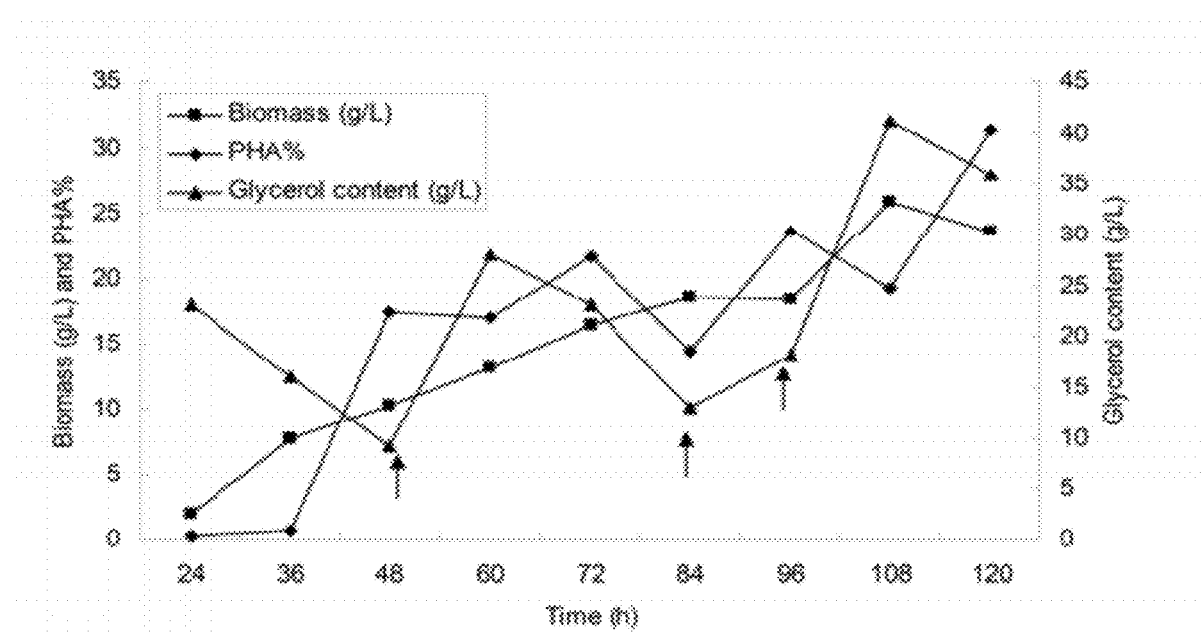
FIG. 7. Changes in biomass, PHA % and glycerol concentration during a fed-batch fermentation, in a 400-L fermentor, with periodic additions (↑) of biodiesel-glycerol. ■ Biomass (g/L). ◆ PHA %. ▲ Glycerol content (g/L). X-axis, Time (h). Left Y-axis, Biomass (g/L) and PHA %. Right Y-axis, Glycerol content (g/L).

The initial evaluation of physical properties of glycerol-based PHB demonstrated the potential application of glycerol as a carbon source to support growth and PHB production by *B. cepacia*. Subsequently, biodiesel-glycerol was used as the carbon source for a 200-L pilot scale fermentation. Dissolved oxygen (DO) and pH were controlled at 35-40% and 7.0, respectively. As shown in FIG. 7, glycerol concentration was kept between 10 g/L and 40 g/L with periodic additions of glycerol. Biomass gradually increased and reached maximum density of 25.8 g/L at 108 h. PHA accumulated quickly from 0.7% at 36 h to 17.4% at 48 h, and PHA % fluctuated near 20% before increasing to the highest point of 31.4% at 120 h. In total, 26.5 L glycerol and 2.5 kg ammonium sulfate were added into the 400-L fermentor in a fed-batch mode and the cells were harvested at 120 h. The final yield of dry biomass and PHB were 23.6 g/L and 7.4 g/L, respectively.

Discussion

Due to environmental pollution caused by relatively recalcitrant plastics and the consumption of fossil fuels for their production, biodegradable PHAs have attracted attention for their unique properties as thermoplastics or elastomers. However, the high cost of PHA production, primarily due to the cost of the feedstock and PHA recovery, has hindered large scale industrial production.

When biodiesel-glycerol was used as the sole carbon source in shake flasks, *B. cepacia* produced 5.8 g/L dry biomass and contained up to 81.9% PHB of total dry biomass when using 3% (v/v) biodiesel-glycerol as a feedstock over 96 h of growth. *B. cepacia* showed higher dry cell weights and PHA production when grown on glycerol when compared to *E. coli* and various Pseudomonads grown on glycerol. (Table 3).

TABLE 3

Comparison of dry cell mass and PHA content from different bacterial strains grown on various carbon sources in shake flasks.

| Bacteria | Substrates | Polymer | Cell weight (g/L) | PHA content (%) | Ref. |
|---|---|---|---|---|---|
| B. cepacia | Glycerol | PHB | 5.8 | 81.9 | Present example |
| B. cepacia | Xylose + Levulinic acid | PHB-co-PHV | 4.4-5.3 | 42-56 | 1 |
| E. coli | Glucose | PHB | 4.9 | 27.6 | 2 |
| E. coli | Glycerol | PHB | 5.6 | 9.8 | 2 |
| E. coli | Glycerol | PHB | 3.6 | 34 | 3 |
| P. corrugata | Glycerol (2%) | PHB | 3.4 | 19.7 | 4 |
| P. oleovorans | Glycerol (1%) | mcl-PHA | 1.9 | 26.8 | 4 |

Table 3 References:
1. Keenan T M, Tanenbaum S W, Stipanovic A J, Nakas J P. Production and characterization of poly-beta-hydroxyalkanoate copolymers from *Burkholderia cepacia* utilizing xylose and levulinic acid. Biotechnol. Prog. 2004; 20:1697-1704.
2. Almeida A D, Nikel P I, Giordano A M, Pettinari M J. Effects of granule-associated protein PhaP on glycerol-dependent growth and polymer production in poly(3-hydroxybutyrate)-producing *Escherichia coli*. Appl. Environ. Microbiol. 2007; 73: 7912-7916.
3. Nikel P, Pettinari J, Mendez B. Poly(3-hydroxybutyrate) synthesis in microaerobic fed-batch cultures by a recombinant *Escherichia coli* arcA mutant using glycerol as a carbon source. J. Biotechnol. 2007; 131:S157-S158.
4. Papanikolaou S, Fakas S, Fick M, Chevalot I, Galiotou-Panayotou M, Komaitis M, Marc I, Aggelis G. Biotechnological valorization of raw glycerol discharged after biodiesel (fatty acid methyl esters) manufacturing process: production of 1,3-propanediol, citric acid and single cell oil. Biomass Bioenergy. 2007; 32:60-71.

However, increasing glycerol concentration from 3% to 9% (FIG. 3) resulted in a decrease of microbial biomass of *B. cepacia* of almost 50%. In a recent study by Cavalheiro et al. (Cavalheiro J M B T, Dealmeida M C M D, Grandfils C, Dafonseca M M R. Poly(3-hydroxybutyrate) production by *Cupriavidus necator* using waste glycerol. Process Biochem. 2009; 44:509-515) similar effects of increasing concentrations of glycerol (on microbial growth) were observed. Specifically, at glycerol concentrations exceeding 30 g·L$^{-1}$, the specific growth rate of *C. necator* decreased when using either pure glycerol or biodiesel-glycerol as sole sources of carbon. In a recent publication by Cavalheiro et al. (Cavalheiro J M B T, Dealmeida M C M D, Grandfils C, Dafonseca M M R. Poly(3-hydroxybutyrate) production by *Cupriavidus necator* using waste glycerol. Process Biochem. 2009; 44:509-515) experiments were performed to establish the effects of gas composition and rate of addition to fed batch cultures of *C. necator*. The authors demonstrated significant increases in dry cellular biomass (g L$^{-1}$) by increasing the flow rate from 1.5 to 3.0 L of air min$^{-1}$. Additionally, exponential phase growth and final cell densities were achieved sooner by aeration with 2.0 L air min$^{-1}$ supplemented with 1.0 L pure oxygen min$^{-1}$. Preliminary experiments for this work established that initially 1 VVM (volume of air per volume of medium per minute) was sufficient to maintain maximum growth. As the fermentation progressed, whenever the dissolved oxygen fell below 35%, the impeller speed and aeration (data not shown) were increased to maintain dissolved oxygen between 35 and 50%. The latter was found to be optimal for cell growth and PHA production by *B. cepacia* and this approach was used in all fermentor experiments.

The molecular mass of PHB varies from 50 to 3,000 kDa (Madison L L, Huisman G W. Metabolic engineering of poly (3-hydroxyalkanoates): from DNA to plastic. *Microbiol Mol Biol Rev.* 1999; 63:21-53; Sudesh K, Abe H, Doi Y. Synthesis, structure and properties of polyhydroxyalkanoates: biological polyesters. *Prog Polym Sci.* 2000; 25:1503-1555), depending on the microorganism and growth conditions. Although the pathways of PHA synthesis using different carbon sources have been previously described (Sudesh K, Abe H, Doi Y. Synthesis, structure and properties of polyhydroxyalkanoates: biological polyesters. *Prog Polym Sci.* 2000; 25:1503-1555; Yeh J I, Chinte U, Du S. Structure of glycerol-3-phosphate dehydrogenase, an essential monotopic membrane enzyme involved in respiration and metabolism. *Proc Natl Acad Sci USA.* 2008; 105:3280-3285), the mechanism for regulating molecular mass in PHA production is still unclear. The activity of PHA synthase (moles of substrate converted per unit time) may influence the molecular mass and the polydispersity of the polymer. It has been shown previously that PHA synthases with higher activity produced lower molecular weight polyesters (Rehm B H, Steinbuchel A. Biochemical and genetic analysis of PHA synthases and other proteins required for PHA synthesis. *Int J Biol Macromol.* 1999; 25:3-19; Sim S J, Snell K D, Hogan S A, Stubbe J, Rha C, Sinskey A J. PHA synthase activity controls the molecular weight and polydispersity of polyhydroxybutyrate in vivo. *Nat Biotechnol.* 1997; 15: 63-67; Gerngross T U, Martin D P. Enzyme-catalyzed synthesis of poly[(R)-(–)-3-hydroxybutyrate]: Formation of macroscopic granules in vitro. *Proc Natl Acad Sci USA.* 1995; 92:6279-6283). On the other hand, enhancing the specific activity of PHA synthase in a phaC mutant increased not only PHA accumulation, but also weight-average molecular weight by 6% to 74% (Amara A A, Steinbuchel A, Rehm B H. In vivo evolution of the *Aeromonas punctata* polyhydroxyalkanoate (PHA) synthase: isolation and characterization of modified PHA synthases with enhanced activity. *Appl Microbiol Biotechnol.* 2002; 59:477-482). Thus, PHA synthase is not the only factor to control and regulate the molecular weight of PHAs, and other enzymes or compounds may also play an important role in chain termination of the polymer.

In addition to providing a carbon source, glycerol has a unique function as a terminal end group for PHB synthesis. Both *Ralstonia eutropha* (formerly *Alcaligenes eutrophus*) and *Pseudomonas oleovorans* are known to produce short-chain-length PHAs; however, when using glycerol as the sole carbon source, the molecular mass of PHB was substantially lower than that produced from glucose and whey sugars (glucose and galactose from lactose hydrolysis) (Koller M, Bona R, Braunegg G, Hermann C, Horvat P, Kroutil M, Martinz J, Neto J, Pereira L, Varila P. Production of polyhydroxyalkanoates from agricultural waste and surplus materials. *Biomacromolecules.* 2005; 6:561-565; Madden L A, Anderson A J, Shah D T, Asrar J. Chain termination in polyhydroxyalkanoate synthesis: involvement of exogenous hydroxy-compounds as chain transfer agents. *Int J Biologl Macromol.* 1999; 25:43-53; Taidi B, Anderson A J, Dawes E A, Byrom D. Effect of carbon source and concentration on the molecular-mass of poly(3-Hydroxybutyrate) produced by *Methylobacterium extorquens* and *Alcaligenes eutrophus*. *Appl Microbiol Biotechnol.* 1994; 40:786-790). The molecular weight gradually decreased as glycerol concentration increased (Ashby R D, Solaiman D K, Foglia T A. Synthesis of short-/medium-chain-length poly(hydroxyalkanoate) blends by mixed culture fermentation of glycerol. *Biomacromolecules.* 2005; 6:2106-2112). In this study, when glycerol content was increased from 3% (v/v) to 9% (v/v), both the molecular weight of PHB and dry cell weight decreased. One possible explanation for this phenomenon is that the organism was inhibited by osmotic stress as the glycerol content increased. The cells began to decrease their enzymatic efficiency and undergo chain termination earlier. PHB was capped by glycerol through covalent esterification in a chain termination position, resulting in lower molecular weights of the polymers produced. As the cells were in contact with glycerol for longer time periods, there was a higher possibility for chain termination to form the lower molecular mass polymers. The osmotic stress may also have caused a slower growth rate and explains the decreasing cell dry weight. Interestingly, there has been no evidence to show that medium-chain-length PHA (produced from *Pseudomonas corrugata*) polymers can be esterified with glycerol to form an end-capped polymer. Perhaps the PHA synthase of strains producing medium-chain-length PHAs (monomers greater than 6 carbons) cannot incorporate small molecules such as glycerol. However, the PHA synthase of *B. cepacia* may more readily incorporate glycerol as a terminal group because the enzyme may exhibit specificity for shorter chain length substrates.

The glycerol-based PHB exhibited similar $T_g$ and $T_m$ compared with PHB polymers produced in cells grown on xylose or compared with commercially available polypropylene.[10] $T_{decomp}$, however, was 13° C. higher in glycerol-capped PHB compared to xylose-based PHB. This advantage could provide a broader range for temperature exposure in certain industrial applications.

Although the thermal properties of the glycerol endcapped PHB in this study were not markedly different from PHB without end-capping, the molecular weights of the polymers were significantly lower. The lower molecular weights of the end-capped polymers may affect the tensile strength of the polymers (Aoyagi Y, Doi Y, Iwata T. Mechanical properties and highly ordered structure of ultra-high-molecular weight poly[(R)-3-hydroxybutyrate] films: effects of annealing and two-step drawing. Polym Degrad Stab. 2003; 79:209-216).

The diol of these end caps can provide a pair of functional groups (—OH) through which these polymers have the potential to be further chemically modified to produce novel PHA derivatives. For example, a cross-linking reagent can be used that reacts, under alkaline conditions, with the free hydroxyl groups of PHAs end-capped with glycerol. One cross linking molecule will bridge two PHB molecules through the hydroxyl groups of the glycerols. The remaining —OH from the end-capped PHB and a newly-formed hydroxyl group from the cross-linking reaction also have the potential to link with other end-capped PHB molecules.

In conclusion, when using glycerol as the carbon source, the concentration of glycerol needs to be strictly controlled. By regulating the glycerol content, different lengths of PHB can be produced to meet the diverse criteria of various industrial and medical applications. These studies provide another degree of regulation in the production of PHB by *B. cepacia*. Previous studies by Keenan et al. (Keenan T M, Tanenbaum S W, Stipanovic A J, Nakas J P. Production and characterization of poly-beta-hydroxyalkanoate copolymers from *Burkholderia cepacia* utilizing xylose and levulinic acid. *Biotechnol Prog.* 2004; 20:1697-1704) have demonstrated the regulation of compositional content (PHB-co-PHV) using xylose and levulinic acid and this investigation describes the regulation of molecular mass by end capping with glycerol.

Example 2

Addition of Talc as a Nucleating Agent to Purified PHAs to Improve their Physical-Chemical Characteristics This example demonstrates the effect of the addition of talc as a nucleating agent on the crystallization temperature of the homopolymer PHB and the copolymer PHB-co-5.6% PHV. Talc was added as a nucleating agent as described in Section 5.4 above.

Figure 8:
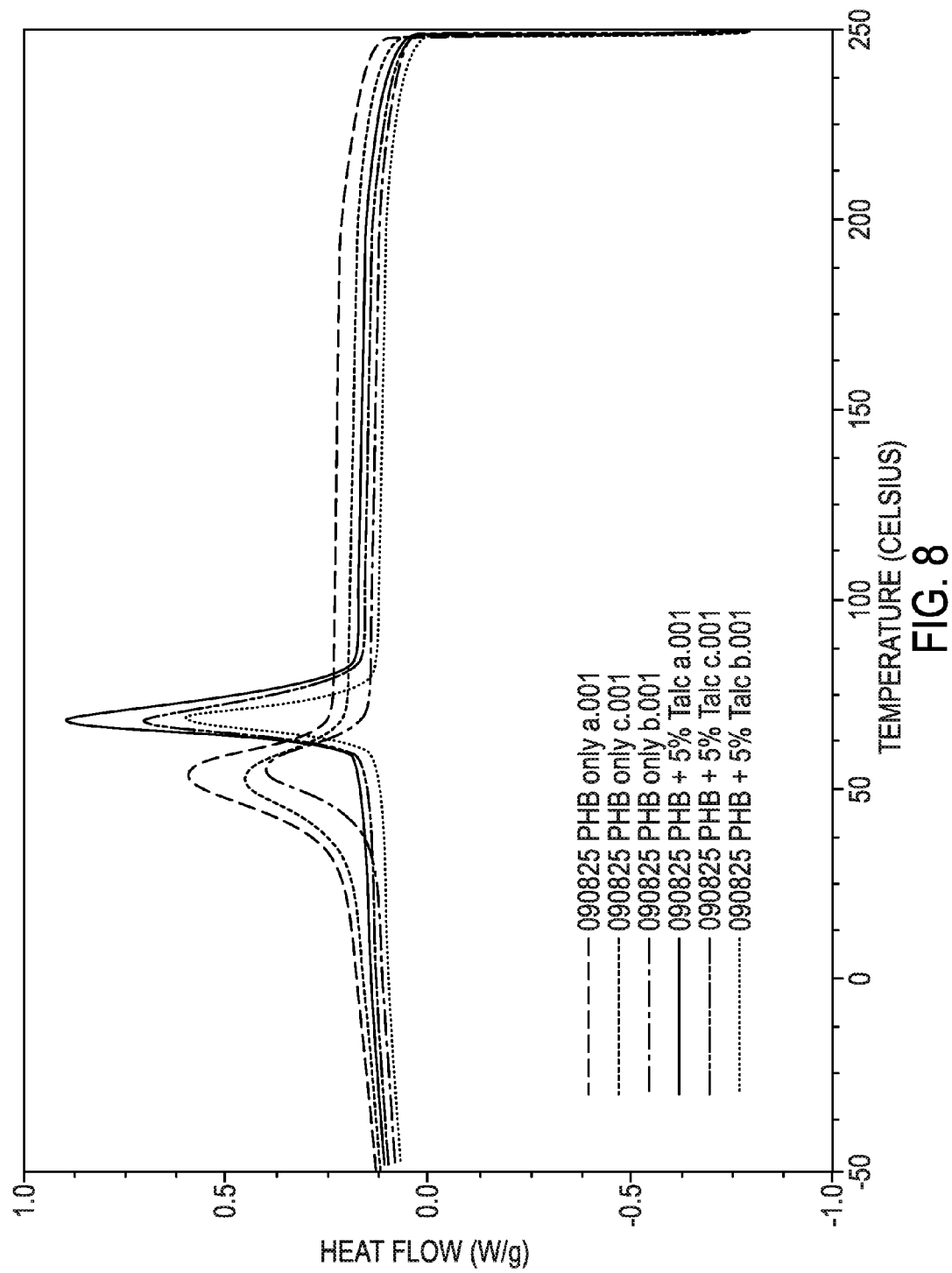
FIG. 8. Effect of 5% talc on crystallization temperature of PHB. The first three peaks, with an average temperature of 53.51° C. (run in triplicate) represent the crystallization temperature for polyhydroxybutyric acid (PHB), without a nucleating agent. The second group of 3 peaks represents the crystallization temperature for PHB in the presence of talc, a nucleating agent, indicating a difference of almost 15° C. Three graph lines labeled "090825 PHB only" represent homopolymer PHB; three graph lines labeled "090825 PHB+5% Talc" represent homopolymer PHB with 5% talc. X-axis, Temperature (Celsius). Y-axis, Heat Flow (W/g).

FIG. 8 shows the crystallization temperature of PHB (• line, triplicate) and PHB with 5% Talc (♦ line, triplicate). With the addition of talc as a nucleating agent, crystallization temperature of the PHB increased by almost 15° C. (from 53.510° C. to 68.420° C.).

Figure 9:
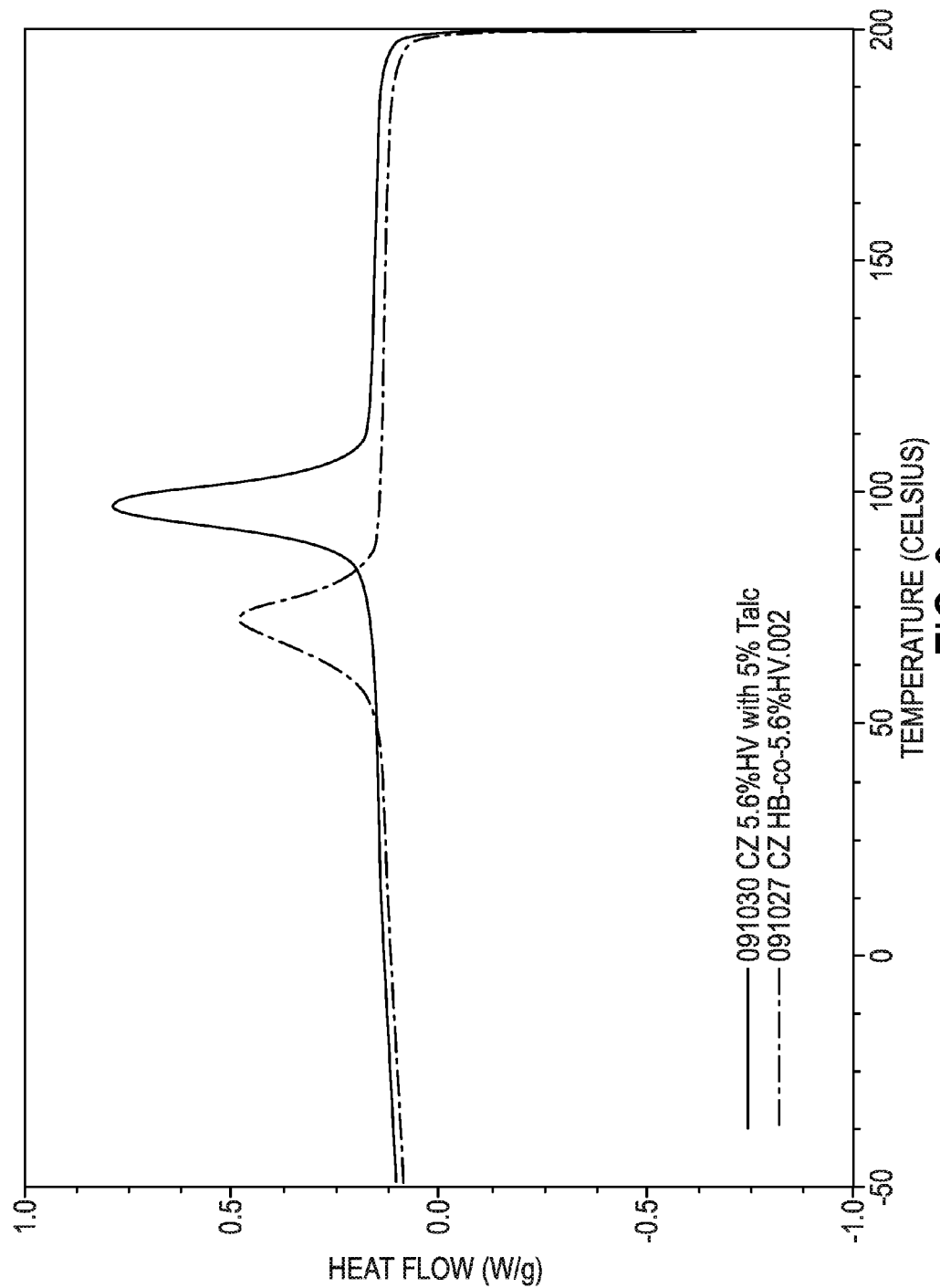
FIG. 9. Effect of Talc on crystallization temperature of PHB-co-5.6% PHV. Graph line labeled "091027 CZ HB-co-5.6% HV.002" represents copolymer PHB-co-5.6% PHV; graph line labeled "091030 CZ 5.6% HV with 5% Talc" represents copolymer PHB-co-5.6% PHV with 5% Talc. X-axis, Temperature (Celsius). Y-axis, Heat Flow (W/g).

FIG. 9 shows the crystallization temperature of PHB-co-5.6% PHV (• line) and PHB-co-5.6% PHV with 5% talc (♦ line). The crystallization temperature of the copolymer increased by almost 25° C. (from 72.32° C. to 97.09° C.).

This observed increase in crystallization temperature is advantageous. The increase in crystallization temperature did not alter the melting temperature so that it approached the decomposition temperature: it did not narrow the range between the melting and decomposition temperatures to such a degree that the temperature for melting the polymer for injection molding, extrusion, fiber spinning, or other melt-related applications would approach the temperature at which the polymer would begin to degrade.

Example 3

Mechanical Properties of PHB-co-Hydroxyvalerate (PHB-co-HV) Copolymers

In this example, the mechanical properties of PHB-co-Hydroxyvalerate (PHB-co-HV) copolymers were characterized using a tensile strength test. PHB-co-HV copolymers demonstrated much better elasticity than the PHB homopolymers.

Materials and Methods

PHB homopolymers and PHB-co-HV copolymers were tested using a tensile strength test. Such tests are well known in the art. The tensile strength test was used to evaluate mechanical properties of PHAs and elucidate more comprehensive material properties in addition to physical properties. The stress ($\sigma$)-strain ($\epsilon$) curve (FIG. 10) show data on the mechanical properties of the tested materials. This includes well known characteristics such as tensile strength, at which the sample is stretched to break; yield strength, at which a material begins to deform plastically and prior to which the material will deform elastically and will return to its original shape when the applied force is removed; Young's Modulus, which displays elasticity and stiffness of the material; and elongation to break, which indicates the strain on a sample when it breaks.

Figure 10:
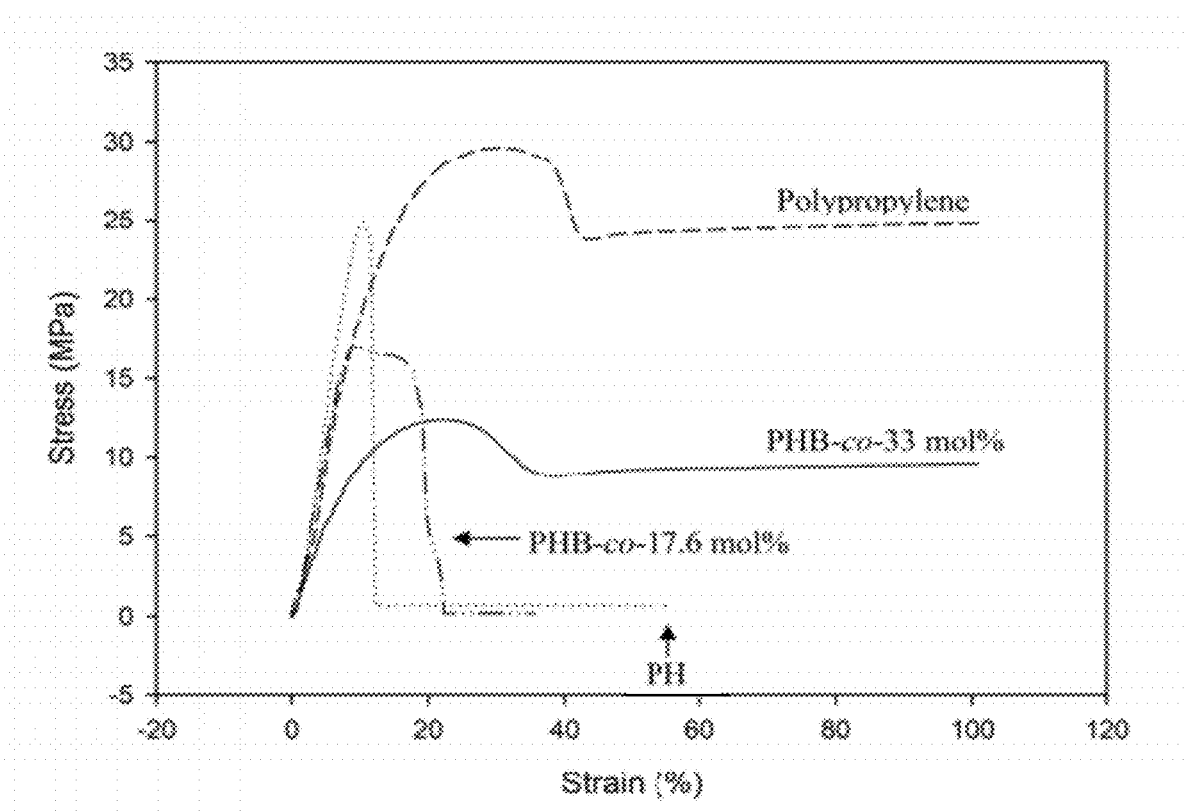
FIG. 10. Stress-strain curves of PHAs and polypropylene. Dotted line: PHB (produced by *B. cepacia* using xylose as a carbon source). Dash-dotted line: PHB-co-17.6 mol % hydroxyvalerate (HV). Solid line: PHB-co-17.6 mol % HV. Dashed line: polypropylene. X-axis, Strain (%). Y-axis, Stress (MPa).

The stress-strain curve begins as a linear relationship and the initial slope of the linear portion is defined as Young's Modulus. If the initial slope, calculated from the curve by statistical regression ($0<\epsilon<10\%$), is larger, the material is more rigid and less elastic. As shown in FIG. 10, the curve for a PHB sample exhibited the sharpest rise at the beginning, corresponding to the highest Young's Modulus, indicating the PHB homopolymer exhibits the greatest rigidity and the least elasticity among these four samples which included two PHB-co-HV copolymers and polypropylene. Meanwhile, the copolymer PHB-co-17.6 mol % HV exhibited similar elasticity to polypropylene due to these two initial curves being almost identical. The copolymer PHB-co-33 mol % HV exhibited the lowest Young's Modulus indicating that it is the most elastic material among these four samples in FIG. 10 under these test conditions.

In addition, visual observation of the polymer samples during stretching at a speed of 100 μm/s demonstrated the apparent difference between the PHB homopolymer and the PHB-co-HV copolymers with various mol % HV. Dogbone-shaped PHB samples at a thickness of 0.4 mm were pulled to break within 10 seconds and exhibited rather limited displacement (low elasticity) (FIG. 11A). As the mol % HV in the copolymer increased, the copolymer dogbones demonstrated better strain without cleavage during stretching, and it usually took several minutes for the copolymers to break (FIG. 11B-C). The copolymer with higher HV mol % thus had better stretchability.

The material properties of each sample were determined by the stress-strain curve and are summarized in Table 4. PHB homopolymer produced from xylose or glycerol as a carbon source exhibited different mechanical properties, possibly due to different molecular masses. Xylose-based PHB with a higher molecular mass exhibited higher tensile strength (26 MPa), slightly higher elasticity (Young's Modulus, 304 MPa) and better elongation to break (12%) than glycerol-derived PHB with lower molecular mass (tensile strength, 17 MPa; Young's Modulus, 277 MPa; elongation to break, 8%). Furthermore, PHB-co-29.5 mol % HV exhibited tremendous improvement of elongation to break (28-fold higher than PHB-co-17.6 mol % HV). Therefore, the copolymer with mol % HV between 17.6 and 29.5 can serve as a good alternative for conventional petroleum-derived plastics.

TABLE 4

Mechanical Properties of PHB, PHB-co-HV Copolymers and Polypropylene

| Mol % HV in PHB-co-HV copolymers | Tensile Strength (MPa) | Yield Strength (MPa) | Young's Modulus (MPa) | Elongation to Break (%) | $M_n^d$ | PDI |
|---|---|---|---|---|---|---|
| 0 (Xylose-based PHB)[a] | 26 ± 1 | 25 ± 1 | 304 ± 32 | 12 ± 1 | 468 | 2.0 |
| 0 (Glycerol-based PHB)[b] | 17 ± 3 | 16 ± 3 | 277 ± 20 | 8 ± 2 | 122 | 2.4 |
| 17.6 | 20 ± 2 | 16 ± 1 | 228 ± 2 | 20 ± 2 | 244 | 2.2 |
| 29.5 | 17 ± 1 | 13 ± 2 | 61 ± 1 | 560 ± 37 | 284 | 2.3 |
| 33.0 | 19 ± 2 | 14 ± 2 | 68 ± 10 | 1046 ± 4 | 205 | 2.6 |
| 35.8 | 19 ± 1 | 10 ± 0.4 | 45 ± 14 | 1058 ± 33 | 280 | 2.1 |
| Polypropylene | >32[c1] | 30 ± 2 | 189 ± 16 | >1067[c2] | / | / |

Note:
[a] and [b] represent PHB produced by *B. cepacia* using xylose or glycerol as a carbon source, respectively.
[c1] and [c2] represent the maximum reading for tensile strength and elongation to break, respectively, under the conditions set for this tensile test (see the tensile test part in Materials and Methods).
[d] represents number average molecular weight in units of KiloDaltons (kDa).

CONCLUSION

In summary, the PHB-co-HV copolymers demonstrated much better elasticity than the PHB homopolymer based on Young's Modulus and elongation to break. For the copolymers, a higher mol fraction of HV resulted in greater elasticity and lower yield strength. In addition, all glycerol-derived PHB and PHB-co-HV exhibited similar tensile strength. Polypropylene, used as a reference, demonstrated higher tensile and yield strength than all PHA samples tested in this study; however, it was less elastic than PHB-co-HV copolymers containing higher than 17.6 mol % of HV, as indicated by Young's Modulus, The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All references cited herein are incorporated herein by reference in their entirety and for all purposes to the same extent as if each individual publication, patent or patent application was specifically and individually indicated to be incorporated by reference in its entirety for all purposes.

The citation of any publication is for its disclosure prior to the filing date and should not be construed as an admission that the present invention is not entitled to antedate such publication by virtue of prior invention.

What is claimed is:

1. A method for producing, by microbial fermentation, polyhydroxyalkanoate (PHA) having an increased elongation-to-break or resistance to breaking, the method comprising the steps of:
    (a) providing a culture medium, wherein the culture medium comprises:
        (i) glycerol as a primary carbon source wherein the glycerol concentration is 3% to 9% (v/v), and
        (ii) levulinic acid as a secondary carbon source;
    (b) culturing a microorganism that converts carbon to PHA in the culture medium;
    (c) harvesting biomass from the culture medium;
    (d) extracting crude PHA from the harvested biomass; and
    (e) purifying PHA from the crude PHA, thereby recovering purified PHA,
wherein the purified PHA:
    has increased elongation-to-break or resistance to breaking, and
    is a medium chain length polymer having the structural formula of:

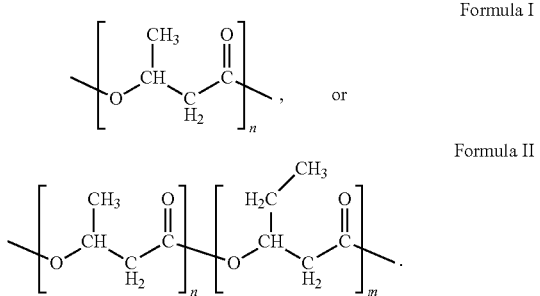

2. The method of claim 1 wherein the glycerol is biodiesel-glycerol.

3. The method of claim 1 comprising, after step (e), the step of:
    (f) adding talc as a nucleating agent to the purified PHA, thereby increasing the crystallization temperature of the purified PHA.

4. The method of claim 3 wherein the added talc concentration is 0.1-1%, 1-5% or 5%-10%.

5. The method of claim 1 wherein the microorganism is selected from the group consisting of *Burkholderia cepacia, Ralstonia eutropha, Alcaligenes latus, Paracoccus denitrificans, Cupriavidus necator, Methylobacterium rhodesianum, Pseudomonas corrugata, Pseudomonas oleovorans* and *Pseudomonas putida*.

6. The method of claim 1 wherein:
    the PHA is a PHA copolymer of a plurality of different monomers in a desired ratio, and
    the ratio of glycerol to the secondary carbon source in the culture medium is predetermined (or sufficient) to produce the desired ratio of different monomers in the PHA copolymer.

7. The method of claim 6 wherein:
    the PHA is a PHA copolymer of butyric acid and valeric acid in a desired ratio,
    the secondary carbon source is levulinic acid, and
    the ratio of glycerol to levulinic acid in the culture medium is predetermined (or sufficient) to produce the desired ratio of butyric acid and valeric acid in the PHA copolymer.

8. The method of claim 1 wherein the increased elongation-to-break or resistance to breaking is from 20±2% to 1058±33%.

9. A method for producing, by microbial fermentation, polyhydroxyalkanoate (PHA) copolymer having an increased elongation-to-break or resistance to breaking, the PHA copolymer comprising a plurality of different monomers, the method comprising the steps of:
    (a) providing a culture medium, wherein the culture medium comprises:
        (i) glycerol as a primary carbon source wherein the glycerol concentration is 3% to 9% (v/v), and
        (ii) levulinic acid as a secondary carbon source,
    wherein the ratio of glycerol to the secondary carbon source in the culture medium is sufficient to produce the desired ratio of different monomers in the PHA copolymer;
    (b) culturing a microorganism that converts carbon to PHA copolymer in the culture medium;
    (c) harvesting biomass from the culture medium;
    (d) extracting crude PHA copolymer from the harvested biomass; and
    (e) purifying PHA copolymer from the crude PHA copolymer, thereby recovering purified PHA copolymer, wherein the purified PHA copolymer
    has increased elongation-to-break or resistance to breaking, and
    is a medium chain length polymer having the structural formula of:

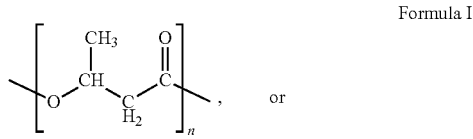

-continued

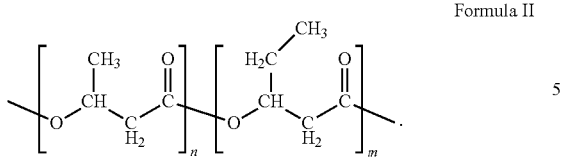

Formula II

10. The method of claim 9, additionally comprising the step of adding talc as a nucleating agent to the purified PHA copolymer, thereby increasing the crystallization temperature of the purified PHA copolymer.

11. The method of claim 9 wherein:
the PHA copolymer is a PHA copolymer of butyric acid and valeric acid in a desired ratio,
the secondary carbon source is levulinic acid, and
the ratio of glycerol to levulinic acid in the culture medium is sufficient to produce the desired ratio of butyric acid and valeric acid in the PHA copolymer.

12. The method of claim 9 wherein the increased elongation-to-break or resistance to breaking is from 20±2% to 1058±33%.

13. The method of claim 9 wherein the microorganism is selected from the group consisting of *Burkholderia cepacia, Ralstonia eutropha, Alcaligenes latus, Paracoccus denitrificans, Cupriavidus necator, Methylobacterium rhodesianum, Pseudomonas corrugata, Pseudomonas oleovorans* and *Pseudomonas putida*.

\* \* \* \* \*